United States Patent
Belevich et al.

(10) Patent No.: US 12,171,621 B2
(45) Date of Patent: *Dec. 24, 2024

(54) CALIBRATION OF MULTIPLE APERTURE ULTRASOUND PROBES

(71) Applicant: MAUI IMAGING, INC., San Jose, CA (US)

(72) Inventors: Artem Belevich, San Jose, CA (US); Josef R. Call, Campbell, CA (US); Bruce R. Ritzi, Sunnyvale, CA (US); Nathan W. Osborn, Palo Alto, CA (US)

(73) Assignee: Maui Imaging, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/675,390

(22) Filed: Feb. 18, 2022

(65) Prior Publication Data

US 2022/0167949 A1    Jun. 2, 2022

Related U.S. Application Data

(63) Continuation of application No. 16/121,303, filed on Sep. 4, 2018, now Pat. No. 11,253,233, which is a
(Continued)

(51) Int. Cl.
*A61B 8/00* (2006.01)
*A61B 6/58* (2024.01)
(Continued)

(52) U.S. Cl.
CPC .............. *A61B 8/587* (2013.01); *A61B 6/584* (2013.01); *A61B 8/12* (2013.01); *A61B 8/4477* (2013.01);
(Continued)

(58) Field of Classification Search
None
See application file for complete search history.

(56) References Cited

U.S. PATENT DOCUMENTS 3,174,286 A    3/1965 Erickson
3,895,381 A    7/1975 Kock
(Continued)

FOREIGN PATENT DOCUMENTS

CN    1535243 A    10/2004
CN    1636150 A    7/2005
(Continued)

OTHER PUBLICATIONS

Abeysekera et al.; Alignment and calibration of dual ultrasound transducers using a wedge phantom; Ultrasound in Medicine and Biology; 37(2); pp. 271-279; Feb. 2011.
(Continued)

*Primary Examiner* — Luke D Ratcliffe
*Assistant Examiner* — Jonathan D Armstrong
(74) *Attorney, Agent, or Firm* — Shay Glenn LLP

(57) ABSTRACT

The quality of ping-based ultrasound imaging is dependent on the accuracy of information describing the precise acoustic position of transmitting and receiving transducer elements. Improving the quality of transducer element position data can substantially improve the quality of ping-based ultrasound images, particularly those obtained using a multiple aperture ultrasound imaging probe, i.e., a probe with a total aperture greater than any anticipated maximum coherent aperture width. Various systems and methods for calibrating element position data for a probe are described.

19 Claims, 8 Drawing Sheets

Related U.S. Application Data continuation of application No. 15/400,826, filed on Jan. 6, 2017, now Pat. No. 10,064,605, which is a continuation of application No. 13/964,701, filed on Aug. 12, 2013, now Pat. No. 9,572,549.

(60) Provisional application No. 61/681,986, filed on Aug. 10, 2012.

(51) Int. Cl.
  *A61B 8/08* (2006.01)
  *A61B 8/12* (2006.01)
  *G01S 7/52* (2006.01)

(52) U.S. Cl.
  CPC .......... *A61B 8/4488* (2013.01); *A61B 8/4494* (2013.01); *A61B 8/483* (2013.01); *G01S 7/52052* (2013.01)

(56) References Cited

U.S. PATENT DOCUMENTS

| | | |
|---|---|---|
| 3,974,692 A | 8/1976 | Hassler |
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 180,792 A | 12/1979 | Lederman et al. |
| 4,205,394 A | 5/1980 | Pickens |
| 4,229,798 A | 10/1980 | Rosie |
| 4,259,733 A | 3/1981 | Taner et al. |
| 4,265,126 A | 5/1981 | Papadofrangakis et al. |
| 4,271,842 A | 6/1981 | Specht et al. |
| 4,325,257 A | 4/1982 | Kino et al. |
| 4,327,738 A | 5/1982 | Green et al. |
| 4,328,569 A | 5/1982 | Trott et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,511,998 A | 4/1985 | Kanda et al. |
| 4,539,847 A | 9/1985 | Paap |
| 4,566,459 A | 1/1986 | Umemura et al. |
| 4,567,768 A | 2/1986 | Satoh et al. |
| 4,604,697 A | 8/1986 | Luthra et al. |
| 4,662,222 A | 5/1987 | Johnson |
| 4,669,482 A | 6/1987 | Ophir |
| 4,682,497 A | 7/1987 | Sasaki |
| 4,694,434 A | 9/1987 | Vonn Ramm et al. |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 4,990,462 A | 2/1991 | Sliwa, Jr. |
| 5,027,658 A | 7/1991 | Anderson |
| 5,050,588 A | 9/1991 | Grey et al. |
| 5,060,205 A | 10/1991 | Phelan |
| 5,062,295 A | 11/1991 | Shakkottai et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,349,960 A | 9/1994 | Gondo |
| 5,355,888 A | 10/1994 | Kendall |
| 5,381,794 A | 1/1995 | Tel et al. |
| 5,398,216 A | 3/1995 | Hall et al. |
| 5,409,010 A | 4/1995 | Beach et al. |
| 5,442,462 A | 8/1995 | Guissin |
| 5,454,372 A | 10/1995 | Banjanin et al. |
| 5,477,858 A | 12/1995 | Norris et al. |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Linuma et al. |
| 5,795,297 A | 8/1998 | Daigle |
| 5,797,845 A | 8/1998 | Barabash et al. |
| 5,798,459 A | 8/1998 | Ohba et al. |
| 5,817,023 A | 10/1998 | Daft |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,871,446 A | 2/1999 | Wilk |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,938,612 A | 8/1999 | Kline-Schoder et al. |
| 5,940,778 A | 8/1999 | Marfurt et al. |
| 5,951,479 A | 9/1999 | Holm et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,190,318 B1 | 2/2001 | Bab et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,224,556 B1 | 5/2001 | Schwartz et al. |
| 6,231,511 B1 | 5/2001 | Bae |
| 6,238,342 B1 | 5/2001 | Feleppa et al. |

(56) References Cited

U.S. PATENT DOCUMENTS

| | | |
|---|---|---|
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,279,399 B1 | 8/2001 | Holm |
| 6,289,230 B1 | 9/2001 | Chaiken et al. |
| 6,299,580 B1 | 10/2001 | Asafusa |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,370,480 B1 | 4/2002 | Gupta et al. |
| 6,373,984 B1 | 4/2002 | Gouge et al. |
| 6,374,185 B1 | 4/2002 | Taner et al. |
| 6,394,955 B1 | 5/2002 | Perlitz |
| 6,423,002 B1 | 7/2002 | Hossack |
| 6,431,175 B1 | 8/2002 | Penner et al. |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,464,637 B1 | 10/2002 | Criton et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,490,477 B1 * | 12/2002 | Zylka ............... A61B 6/583 600/417 |
| 6,499,536 B1 | 12/2002 | Ellingsen |
| 6,503,204 B1 | 1/2003 | Sumanaweera et al. |
| 6,508,768 B1 | 1/2003 | Hall et al. |
| 6,508,770 B1 | 1/2003 | Cai |
| 6,514,205 B1 | 2/2003 | Lee et al. |
| 6,517,484 B1 * | 2/2003 | Wilk ............... A61B 8/4209 600/443 |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,582,367 B1 | 6/2003 | Robinson et al. |
| 6,585,647 B1 | 7/2003 | Winder |
| 6,597,171 B2 | 7/2003 | Hurlimann et al. |
| 6,604,421 B1 | 8/2003 | Li |
| 6,614,560 B1 | 9/2003 | Silverbrook |
| 6,620,101 B2 | 9/2003 | Azzam et al. |
| 6,629,929 B1 | 10/2003 | Jago et al. |
| 6,645,147 B1 | 11/2003 | Jackosn et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,704,692 B1 | 3/2004 | Banerjee et al. |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,835,178 B1 | 12/2004 | Wilson et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,865,140 B2 | 3/2005 | Thomenius et al. |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,293,462 B2 | 11/2007 | Lee et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,764,984 B2 | 7/2010 | Desmedt et al. |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,880,154 B2 | 2/2011 | Otto |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,265,175 B2 | 9/2012 | Barsoum et al. |
| 8,277,383 B2 | 10/2012 | Specht |
| 8,279,705 B2 | 10/2012 | Choi et al. |
| 8,343,054 B1 | 1/2013 | Tamura |
| 8,412,307 B2 | 4/2013 | Willis et al. |

(56) References Cited

U.S. PATENT DOCUMENTS

| | | |
|---|---|---|
| 8,414,564 B2 | 4/2013 | Goldshleger et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,483,804 B2 | 7/2013 | Hsieh et al. |
| 8,532,951 B2 | 9/2013 | Roy et al. |
| 8,539,838 B2 | 9/2013 | Yoo et al. |
| 8,582,848 B2 | 11/2013 | Funka-Lea et al. |
| 8,602,993 B2 | 12/2013 | Specht et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 8,684,936 B2 | 4/2014 | Specht |
| 8,852,103 B2 * | 10/2014 | Rothberg ............... A61N 7/02 600/459 |
| 9,036,887 B2 | 5/2015 | Fouras et al. |
| 9,072,495 B2 | 7/2015 | Specht |
| 9,128,032 B2 * | 9/2015 | Carson ............... G01N 29/30 |
| 9,146,313 B2 | 9/2015 | Specht et al. |
| 9,176,078 B2 | 11/2015 | Flohr et al. |
| 9,192,355 B2 | 11/2015 | Specht et al. |
| 9,217,660 B2 | 12/2015 | Zlotnick et al. |
| 9,220,478 B2 | 12/2015 | Smith et al. |
| 9,247,874 B2 | 2/2016 | Kumar et al. |
| 9,247,926 B2 | 2/2016 | Smith et al. |
| 9,265,484 B2 | 2/2016 | Brewer et al. |
| 9,268,777 B2 | 2/2016 | Lu et al. |
| 9,271,661 B2 | 3/2016 | Moghari et al. |
| 9,277,861 B2 | 3/2016 | Kowal et al. |
| 9,282,945 B2 | 3/2016 | Smith et al. |
| 9,339,256 B2 * | 5/2016 | Specht ............... G01S 15/8922 |
| 9,392,986 B2 | 7/2016 | Ning et al. |
| 9,420,994 B2 | 8/2016 | Specht |
| 9,510,806 B2 | 12/2016 | Smith et al. |
| 9,526,475 B2 | 12/2016 | Specht et al. |
| 9,572,549 B2 | 2/2017 | Belevich et al. |
| 9,576,354 B2 | 2/2017 | Fouras et al. |
| 9,582,876 B2 | 2/2017 | Specht |
| 9,606,206 B2 | 3/2017 | Boernert et al. |
| 9,659,152 B2 | 5/2017 | Mueller |
| 9,668,714 B2 | 6/2017 | Call et al. |
| 9,775,511 B2 | 10/2017 | Kumar et al. |
| 9,788,813 B2 | 10/2017 | Adam et al. |
| 9,883,848 B2 | 2/2018 | Specht et al. |
| 9,986,969 B2 | 6/2018 | Call et al. |
| 9,986,975 B2 | 6/2018 | Specht et al. |
| 10,064,605 B2 * | 9/2018 | Belevich ............... A61B 8/12 |
| 10,130,333 B2 | 11/2018 | Specht |
| 10,206,662 B2 | 2/2019 | Smith et al. |
| 10,226,234 B2 | 3/2019 | Specht et al. |
| 10,267,913 B2 | 4/2019 | Smith et al. |
| 10,342,518 B2 | 7/2019 | Specht et al. |
| 10,380,399 B2 | 8/2019 | Call et al. |
| 10,401,493 B2 | 9/2019 | Call et al. |
| 10,617,384 B2 | 4/2020 | Brewer et al. |
| 10,653,392 B2 | 5/2020 | Specht et al. |
| 10,675,000 B2 | 6/2020 | Specht et al. |
| 10,695,027 B2 | 6/2020 | Call et al. |
| 10,835,208 B2 | 11/2020 | Smith et al. |
| 10,856,846 B2 | 12/2020 | Davies et al. |
| 10,925,577 B2 | 2/2021 | Adam et al. |
| 11,016,191 B2 | 5/2021 | Call et al. |
| 11,051,791 B2 | 7/2021 | Smith et al. |
| 11,068,689 B2 | 7/2021 | Call et al. |
| 11,096,662 B2 | 8/2021 | Specht |
| 11,172,911 B2 | 11/2021 | Call et al. |
| 11,253,233 B2 | 2/2022 | Belevich et al. |
| 11,464,492 B2 | 10/2022 | Specht et al. |
| 2002/0035864 A1 | 3/2002 | Paltieli et al. |
| 2002/0073781 A1 | 6/2002 | Hashimoto et al. |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0007598 A1 | 1/2003 | Wang et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0163271 A1 * | 8/2003 | Chell ............... A61B 6/4028 702/107 |
| 2003/0167142 A1 * | 9/2003 | Chell ............... G01S 7/5205 702/107 |
| 2003/0181806 A1 * | 9/2003 | Medan ............... A61B 17/2255 600/411 |
| 2003/0220554 A1 | 11/2003 | Grenon et al. |
| 2003/0228053 A1 | 12/2003 | Li et al. |
| 2004/0015079 A1 | 1/2004 | Berger et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0215075 A1 | 10/2004 | Zagzebski et al. |
| 2004/0236217 A1 | 11/2004 | Cerwin et al. |
| 2004/0236223 A1 | 11/2004 | Barnes et al. |
| 2004/0258127 A1 | 12/2004 | Ramamurthy et al. |
| 2004/0267132 A1 | 12/2004 | Podany |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0061536 A1 | 3/2005 | Proulx |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0148874 A1 | 7/2005 | Brock-Fisher et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0036170 A1 | 2/2006 | Lachaine et al. |
| 2006/0058664 A1 | 3/2006 | Barthe et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0256231 A1 | 11/2006 | Sasaki et al. |
| 2006/0262961 A1 | 11/2006 | Holsing et al. |
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0043290 A1 | 2/2007 | Goepp et al. |
| 2007/0055155 A1 | 3/2007 | Owen et al. |
| 2007/0073781 A1 | 3/2007 | Adkins et al. |
| 2007/0078345 A1 | 4/2007 | Mo et al. |
| 2007/0083109 A1 | 4/2007 | Ustuner et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |

(56) References Cited

U.S. PATENT DOCUMENTS

| | | |
|---|---|---|
| 2008/0009739 A1 | 1/2008 | Chiang et al. |
| 2008/0044572 A1 | 2/2008 | Loeffler et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0132790 A1 | 6/2008 | Burton |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0262357 A1 | 10/2008 | Wodnicki |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2008/0319318 A1 | 12/2008 | Johnson et al. |
| 2009/0005679 A1* | 1/2009 | Dala-Krishna ...... A61B 8/5284 600/437 |
| 2009/0010459 A1 | 1/2009 | Garbini et al. |
| 2009/0012393 A1 | 1/2009 | Choi |
| 2009/0015665 A1 | 1/2009 | Willsie |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0079299 A1 | 3/2009 | Bradley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182233 A1 | 7/2009 | Wodnicki |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0036258 A1 | 2/2010 | Dietz et al. |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0085383 A1 | 4/2010 | Cohen et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0145195 A1 | 6/2010 | Hyun |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0174198 A1 | 7/2010 | Young et al. |
| 2010/0191110 A1 | 7/2010 | Insana et al. |
| 2010/0217124 A1 | 8/2010 | Cooley |
| 2010/0217125 A1 | 8/2010 | Kadokura et al. |
| 2010/0228126 A1 | 9/2010 | Emery et al. |
| 2010/0240994 A1 | 9/2010 | Zheng |
| 2010/0249570 A1* | 9/2010 | Carson ............... G01N 29/2418 600/407 |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0286525 A1 | 11/2010 | Osumi |
| 2010/0286527 A1 | 11/2010 | Cannon et al. |
| 2010/0298712 A1 | 11/2010 | Pelissier et al. |
| 2010/0310143 A1 | 12/2010 | Rao et al. |
| 2010/0317971 A1 | 12/2010 | Fan et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178441 A1 | 7/2011 | Tyler |
| 2011/0196237 A1 | 8/2011 | Pelissier et al. |
| 2011/0213244 A1 | 9/2011 | Frinking et al. |
| 2011/0270088 A1 | 11/2011 | Shiina |
| 2011/0301470 A1 | 12/2011 | Sato et al. |
| 2011/0306886 A1 | 12/2011 | Daft et al. |
| 2011/0319764 A1 | 12/2011 | Okada et al. |
| 2012/0004545 A1 | 1/2012 | Ziv-Ari et al. |
| 2012/0035482 A1 | 2/2012 | Kim et al. |
| 2012/0036934 A1 | 2/2012 | Kröning et al. |
| 2012/0071710 A1 | 3/2012 | Gazdzinski |
| 2012/0085173 A1 | 4/2012 | Papadopoulos et al. |
| 2012/0095343 A1* | 4/2012 | Smith ................. A61B 8/4494 600/447 |
| 2012/0101378 A1 | 4/2012 | Lee |
| 2012/0114210 A1 | 5/2012 | Kim et al. |
| 2012/0121150 A1 | 5/2012 | Murashita |
| 2012/0137778 A1 | 6/2012 | Kitazawa et al. |
| 2012/0140595 A1 | 6/2012 | Amemiya |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0209150 A1 | 8/2012 | Zeng et al. |
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2012/0283564 A1 | 11/2012 | Ebbini et al. |
| 2013/0030296 A1 | 1/2013 | Miyaki |
| 2013/0046168 A1 | 2/2013 | Sui |
| 2013/0070062 A1 | 3/2013 | Fouras et al. |
| 2013/0076207 A1 | 3/2013 | Krohn et al. |

(56) References Cited

U.S. PATENT DOCUMENTS

| | | |
|---|---|---|
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0116561 A1 | 5/2013 | Rothberg et al. |
| 2013/0128702 A1 | 5/2013 | Degertekin et al. |
| 2013/0131516 A1 | 5/2013 | Katsuyama |
| 2013/0144165 A1 | 6/2013 | Ebbini et al. |
| 2013/0204136 A1 | 8/2013 | Duric et al. |
| 2013/0204137 A1 | 8/2013 | Roy et al. |
| 2013/0218012 A1* | 8/2013 | Specht ............ G01S 15/8929 367/7 |
| 2013/0237799 A1* | 9/2013 | Motoki ............ A61B 5/708 600/407 |
| 2013/0258805 A1 | 10/2013 | Hansen et al. |
| 2013/0261463 A1 | 10/2013 | Chiang et al. |
| 2013/0310688 A1 | 11/2013 | Rosen et al. |
| 2013/0317331 A1* | 11/2013 | Bechtel ............ A61B 5/1455 600/323 |
| 2013/0338474 A9* | 12/2013 | Carson ............ A61B 5/0095 600/407 |
| 2013/0345566 A1 | 12/2013 | Weitzel et al. |
| 2014/0073921 A1 | 3/2014 | Specht et al. |
| 2014/0086014 A1 | 3/2014 | Kobayashi |
| 2014/0147013 A1 | 5/2014 | Shandas et al. |
| 2014/0243673 A1 | 8/2014 | Anand et al. |
| 2015/0045668 A1 | 2/2015 | Smith et al. |
| 2016/0223632 A1* | 8/2016 | Baek ............ G01R 33/4625 |
| 2018/0153511 A1 | 6/2018 | Specht et al. |
| 2019/0200961 A1 | 7/2019 | Specht et al. |
| 2020/0275910 A1 | 9/2020 | Specht et al. |
| 2020/0297320 A1 | 9/2020 | Specht et al. |
| 2020/0323513 A1 | 10/2020 | Call et al. |
| 2021/0068787 A1 | 3/2021 | Smith et al. |
| 2021/0085292 A1 | 3/2021 | Davis et al. |
| 2021/0278531 A1 | 9/2021 | Call et al. |
| 2021/0350101 A1 | 11/2021 | Call et al. |
| 2021/0378633 A1 | 12/2021 | Specht et al. |
| 2022/0071601 A1 | 3/2022 | Call et al. |
| 2023/0277158 A1 | 9/2023 | Brewer et al. |
| 2023/0380805 A1 | 11/2023 | Specht et al. |
| 2024/0081787 A1 | 3/2024 | Specht et al. |

FOREIGN PATENT DOCUMENTS

| | | |
|---|---|---|
| CN | 1781460 A | 6/2006 |
| CN | 101103927 A | 1/2008 |
| CN | 101116622 A | 2/2008 |
| CN | 101190134 A | 6/2008 |
| CN | 101453955 A | 6/2009 |
| CN | 100545650 C | 9/2009 |
| CN | 101609150 A | 12/2009 |
| CN | 101852773 A | 6/2010 |
| CN | 101785684 A | 7/2010 |
| CN | 101843501 A | 9/2010 |
| CN | 101912278 A | 12/2010 |
| CN | 101965232 A | 2/2011 |
| CN | 102018533 A | 4/2011 |
| CN | 102112047 A | 6/2011 |
| CN | 102123668 A | 7/2011 |
| CN | 102258388 A | 11/2011 |
| CN | 102283679 A | 12/2011 |
| CN | 102599930 A | 7/2012 |
| CN | 104080407 A | 10/2014 |
| CN | 104105449 A | 10/2014 |
| CN | 104620128 A | 5/2015 |
| DE | 102011114333 A1 | 3/2013 |
| EP | 1346689 A2 * | 9/2003 ............ A61B 6/032 |
| EP | 1944070 A1 | 7/2008 |
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2319417 A1 | 5/2011 |
| EP | 2325672 A1 | 5/2011 |
| EP | 1462819 B1 | 7/2011 |
| EP | 2356941 A1 | 8/2011 |
| EP | 1979739 B1 | 10/2011 |
| EP | 2385391 A2 | 11/2011 |
| EP | 2294400 B1 | 2/2012 |
| EP | 2453256 A2 | 5/2012 |
| EP | 1840594 B1 | 6/2012 |
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | 49-11189 A | 1/1974 |
| JP | 54-44375 A | 4/1979 |
| JP | 55-103839 A | 8/1980 |
| JP | 57-31848 A | 2/1982 |
| JP | 58-223059 A | 12/1983 |
| JP | 59-101143 A | 6/1984 |
| JP | 59-174151 A | 10/1984 |
| JP | 60-13109 U | 1/1985 |
| JP | 60-68836 A | 4/1985 |
| JP | 01164354 A | 6/1989 |
| JP | 02501431 A | 5/1990 |
| JP | 03015455 A | 1/1991 |
| JP | 03126443 A | 5/1991 |
| JP | 04017842 A | 1/1992 |
| JP | 04067856 A | 3/1992 |
| JP | 05042138 A | 2/1993 |
| JP | H05146437 A | 6/1993 |
| JP | 06125908 A | 5/1994 |
| JP | 06254092 A | 9/1994 |
| JP | 07051266 A | 2/1995 |
| JP | 07204201 A | 8/1995 |
| JP | H07204202 A | 8/1995 |
| JP | 08154930 A | 6/1996 |
| JP | 08252253 A | 10/1996 |
| JP | H0315455 A | 1/1997 |
| JP | 09103429 A | 4/1997 |
| JP | 09201361 A | 8/1997 |
| JP | 2777197 B | 5/1998 |
| JP | 10216128 A | 8/1998 |
| JP | 11089833 A | 4/1999 |
| JP | 11239578 A | 9/1999 |
| JP | 2001507794 A | 6/2001 |
| JP | 2001245884 A | 9/2001 |
| JP | 2002209894 A | 7/2002 |
| JP | 2002253548 A | 9/2002 |
| JP | 2002253549 A | 9/2002 |
| JP | 2003235839 A | 8/2003 |
| JP | 2003290224 A | 10/2003 |
| JP | 2004167092 A | 6/2004 |
| JP | 2004215987 A | 8/2004 |
| JP | 2004337457 A | 12/2004 |
| JP | 2004340809 A | 12/2004 |
| JP | 2004351214 A | 12/2004 |
| JP | 2005046192 A | 2/2005 |
| JP | 2005046193 A | 2/2005 |
| JP | 2005152187 A | 6/2005 |
| JP | 2005523792 A | 8/2005 |
| JP | 2005526539 A | 9/2005 |
| JP | 2006051356 A | 2/2006 |
| JP | 2006061203 A | 3/2006 |
| JP | 2006122657 A | 5/2006 |
| JP | 2006130313 A | 5/2006 |
| JP | 2006204923 A | 8/2006 |
| JP | 2007325937 A | 12/2007 |
| JP | 2008122209 A | 5/2008 |
| JP | 2008513763 A | 5/2008 |
| JP | 2008515557 A | 5/2008 |
| JP | 2008132342 A | 6/2008 |
| JP | 2008522642 A | 7/2008 |
| JP | 2008259541 A | 10/2008 |
| JP | 2008279274 A | 11/2008 |
| JP | 2008307087 A | 12/2008 |
| JP | 2009178448 A | 8/2009 |
| JP | 2009240667 A | 10/2009 |

(56) References Cited

FOREIGN PATENT DOCUMENTS

| | | |
|---|---|---|
| JP | 2010005375 A | 1/2010 |
| JP | 2010124842 A | 6/2010 |
| JP | 2010526626 A | 8/2010 |
| JP | 2010227503 A | 10/2010 |
| JP | 2011527586 A | 11/2011 |
| JP | 2011529362 A | 12/2011 |
| JP | 2013118984 A | 6/2013 |
| JP | 2013121493 A | 6/2013 |
| JP | 2014087448 A | 5/2014 |
| JP | 2015500062 A | 1/2015 |
| JP | 2018118081 A | 8/2018 |
| JP | 2020014857 A | 1/2020 |
| KR | 100715132 B | 4/2007 |
| KR | 1020080044737 A | 5/2008 |
| KR | 1020090009258 A | 1/2009 |
| KR | 1020090103408 A | 10/2009 |
| KR | 1020100051108 A | 5/2010 |
| KR | 1020130060875 A | 6/2013 |
| KR | 1020130089645 A | 8/2013 |
| KR | 1020140034114 A | 3/2014 |
| KR | 1020140069664 A | 6/2014 |
| KR | 1020140098843 A | 8/2014 |
| WO | WO92/18054 A1 | 10/1992 |
| WO | WO98/00719 A2 | 1/1998 |
| WO | WO01/64109 A1 | 9/2001 |
| WO | WO02/17296 A1 | 2/2002 |
| WO | WO02/084594 A2 | 10/2002 |
| WO | WO2005/009245 A1 | 2/2005 |
| WO | WO2006/113445 A1 | 10/2006 |
| WO | WO2006/114735 A1 | 11/2006 |
| WO | WO2007/013814 A2 | 2/2007 |
| WO | WO2007/127147 A2 | 11/2007 |
| WO | WO2008/097479 A1 | 8/2008 |
| WO | WO2008/127927 A1 | 10/2008 |
| WO | WO2008/137030 A1 | 11/2008 |
| WO | WO2009/060182 A2 | 5/2009 |
| WO | WO2010/095094 A1 | 8/2010 |
| WO | WO2010/137453 A1 | 12/2010 |
| WO | WO2010/139519 A1 | 12/2010 |
| WO | WO2011/004661 A1 | 1/2011 |
| WO | WO2011/057252 A1 | 5/2011 |
| WO | WO2011/064688 A1 | 6/2011 |
| WO | WO2011/094585 A | 8/2011 |
| WO | WO2011/100697 A1 | 8/2011 |
| WO | WO2011/123529 A1 | 10/2011 |
| WO | WO2012/028896 A1 | 3/2012 |
| WO | WO2012/033093 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/112540 A2 | 8/2012 |
| WO | WO2012/131340 A2 | 10/2012 |
| WO | WO2012/160541 A2 | 11/2012 |
| WO | WO2013/030556 A1 | 3/2013 |
| WO | WO2013/059358 A2 | 4/2013 |
| WO | WO2013/109965 A1 | 7/2013 |
| WO | WO2013/116807 A1 | 8/2013 |
| WO | WO2013/116809 A1 | 8/2013 |
| WO | WO2013/116851 A1 | 8/2013 |
| WO | WO2013/116854 A1 | 8/2013 |
| WO | WO2013/116866 A1 | 8/2013 |
| WO | WO2013/126559 A1 | 8/2013 |
| WO | WO2013/128301 A2 | 9/2013 |

OTHER PUBLICATIONS

Arigovindan et al.; Full motion and flow field recovery from echo doppler data; IEEE Transactions on Medical Imaging; 26(1); pp. 31-45; Jan. 2007.

Capineri et al.; A doppler system for dynamic vector velocity maps; Ultrasound in Medicine & Biology; 28(2); pp. 237-248; Feb. 28, 2002.

Carson et al.; Measurement of photoacoustic transducer position by robotic source placement and nonlinear parameter estimation; Biomedical Optics (BIOS): International Society for Optics and Photonics (9th Conf. on Biomedical Thermoacoustics, Optoacoustics, and Acousto-optics; vol. 6856; 9 pages; Feb. 28, 2008.

Chen et al.; Maximum-likelihood source localization and unknown sensor location estimation for wideband signals in the near-field; IEEE Transactions on Signal Processing; 50(8); pp. 1843-1854; Aug. 2002.

Chen et al.; Source localization and tracking of a wideband source using a randomly distributed beamforming sensor array; International Journal of High Performance Computing Applications; 16(3); pp. 259-272; Fall 2002.

Cristianini et al.; An Introduction to Support Vector Machines; Cambridge University Press; pp. 93-111; Mar. 2000.

Dunmire et al.; A brief history of vector doppler; Medical Imaging 2001; International Society for Optics and Photonics; pp. 200-214; May 30, 2001.

Dunmire et al.; Cross-beam vector Doppler ultrasound for angle-independent velocity measurements; Ultrasound in medicine & biology; 26(8); pp. 1213-1235; Oct. 2000.

Du et al.; User parameter free approaches to multistatic adaptive ultrasound imaging; 5th IEEE International Symposium; pp. 1287-1290, May 2008.

Feigenbaum, Harvey, M.D.; Echocardiography; Lippincott Williams & Wilkins; Philadelphia; 5th Ed.; pp. 482, 484; Feb. 1994.

Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.

Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.

Gran et al.; Directional velocity estimation using a spatio-temporal encoding technique based on frequency division for synthetic transmit aperture ultrasound; IEEE transactions on ultrasonics, ferroelectrics, and frequency control; 53(7); pp. 1289-1299; Aug. 2006.

Haykin, Simon; Neural Networks: A Comprehensive Foundation (2nd Ed.); Prentice Hall; pp. 156-187; Jul. 16, 1998.

Heikkila et al.; A four-step camera calibration procedure with implicit image correction; Proceedings IEEE Computer Scociety Conference on Computer Vision and Pattern Recognition, San Juan; pp. 1106-1112; Jun. 17-19, 1997.

Hendee et al.; Medical Imaging Physics; Wiley-Liss, Inc. 4th Edition; Chap. 19-22; pp. 303-353; (year of pub. sufficiently earlier than effective US filing date and any foreign priority date) © 2002.

Hsu et al.; Real-time freehand 3D ultrasound calibration; CUED/F-INFENG/TR 565; Department of Engineering, University of Cambridge, United Kingdom; 14 pages; Sep. 2006.

Jeffs; Beamforming: a brief introduction; Brigham Young University; 14 pages; retrieved from the internet (http://ens.ewi.tudelft.nl/Education/courses/et4235/Beamforming.pdf); Oct. 2004.

Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.

Kramb et al.,.; Considerations for using phased array ultrasonics in a fully automated inspection system. Review of Quantitative Nondestructive Evaluation, 2004 Edition, ed. D. O. Thompson and D. E. Chimenti, American Inst. of Physics, pp. 817-825, Mar. 2004.

Ledesma-Carbayo et al.; Spatio-temporal nonrigid registration for ultrasound cardiac motion estimation; IEEE Trans. on Medical Imaging; vol. 24; No. 9; Sep. 2005.

Leotta et al.; Quantitative three-dimensional echocardiography by rapid imaging . . . ; J American Society of Echocardiography; vol. 10; No. 8; pp. 830-839; Oct. 1997.

Li et al.; An efficient speckle tracking algorithm for ultrasonic imaging; 24; pp. 215-228; Oct. 1, 2002.

Morrison et al.; A probabilistic neural network based image segmentation network for magnetic resonance images; Proc. Conf. Neural Networks; Baltimore, MD; vol. 3; pp. 60-65; Jun. 1992.

(56) References Cited

OTHER PUBLICATIONS

Nadkarni et al.; Cardiac motion synchronization for 3D cardiac ultrasound imaging; Ph.D. Dissertation, University of Western Ontario; Jun. 2002.

Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.

Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.

Saad et al.; Computer vision approach for ultrasound doppler angle estimation; Journal of Digital Imaging; 22(6); pp. 681-688; Dec. 1, 2009.

Sakas et al.; Preprocessing and vol. rendering of 3D ultrasonic data; IEEE Computer Graphics and Applications; pp. 47-54, Jul. 1995.

Sapia et al.; Deconvolution of ultrasonic waveforms using an adaptive wiener filter; Review of Progress in Quantitative Nondestructive Evaluation; vol. 13A; Plenum Press; pp. 855-862; Jan. 1994.

Sapia et al.; Ultrasound image deconvolution using adaptive inverse filtering; 12 IEEE Symposium on Computer-Based Medical Systems, CBMS, pp. 248-253; Jun. 1999.

Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.

Scabia et al.; A real-time two-dimensional pulsed-wave Doppler system; Ultrasound in medicine & biology; 26(1); pp. 121-131; Jan. 1, 2000.

Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.

Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.

Specht et al.; Deconvolution techniques for digital longitudinal tomography; SPIE; vol. 454; presented at Application of Optical Instrumentation in Medicine XII; pp. 319-325; Jun. 1984.

Specht et al.; Experience with adaptive PNN and adaptive GRNN; Proc. IEEE International Joint Conf. on Neural Networks; vol. 2; pp. 1203-1208; Orlando, FL; Jun. 1994.

Specht, D.F.; A general regression neural network; IEEE Trans. on Neural Networks; vol. 2.; No. 6; Nov. 1991.

Specht, D.F.; Blind deconvolution of motion blur using LMS inverse filtering; Lockheed Independent Research (unpublished); Jun. 23, 1975.

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; Feb. 1990.

STERN; The basic concepts of diagnostic ultrasound. Yale-New Haven Teachers Institute; Apr. 2005.

UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.

Urban et al.; Implementation of vibro-acoustography on a clinical ultrasound system; IEEE Transactions on Ultrasonics, Ferroelectrics, and Frequency Control; 58(6); pp. 1169-1181 (Author Manuscript, 25 pgs. ); Jun. 2011.

Urban et al.; Implementation of vibro-acoustography on a clinical ultrasound system; IEEE Ultrasonics Symposium (IUS); pp. 326-329; Oct. 14, 2010.

Von Ramm et al.; High-speed ultrasound volumetric imaging—System. 2. Parallel processing and image display; IEEE Trans. Ultrason., Ferroelect., Freq. Contr.; vol. 38; pp. 109-115; Mar. 1991.

Wang et al.; Photoacoustic tomography of biological tissues with high cross-section resolution: reconstruction and experiment; Medical Physics; 29(12); pp. 2799-2805; Dec. 2002.

Wells, P.N.T.; Biomedical ultrasonics; Academic Press; London, New York, San Francisco; pp. 124-125; Mar. 1977.

Widrow et al.; Adaptive signal processing; Prentice-Hall; Englewood Cliffs, NJ; pp. 99-116; Mar. 1985.

Wikipedia; Point cloud; 2 pages; retrieved Nov. 24, 2014 from the internet (https://en.wikipedia.org/w/index.php?title=Point_cloud&oldid=472583138).

Wikipedia; Curve fitting; 5 pages; retrieved from the internet (http:en.wikipedia.org/wiki/Curve_fitting) Dec. 19, 2010.

Wikipedia; Speed of sound; 17 pages; retrieved from the internet (http:en.wikipedia.org/wiki/Speed_of_sound) Feb. 15, 2011.

Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.

Zhang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.

Spechit et al.; U.S. Appl. No. 17/936,420 entitled "Point source transmission and speed-of-sound correction using multi-aperture ultrasound imaging," filed Sep. 23, 2022.

Bajikar et al.; U.S. Appl. No. 18/165,276 entitled "Multiple aperture ultrasound imaging systems and methods," filed Feb. 6, 2023.

Jensen et al.; Synthetic aperture ultrasound imaging; Ultrasonics; vol. 44; pp. e5-e15; Dec. 22, 2006.

Pinghua; Optimization of Key Parameters of Phased array Ultrasonic Testing; Dalian University of Technology; Masters Dissertation; No. 7; retrieved from the internet (http://www.cnki.net); 69 pages; Jul. 15, 2012.

Call et al.; U.S. Appl. No. 18/330,699 entitled "Network-based ultrasound imaging system," filed Jun. 7, 2023.

Atmeh et al.; U.S. Appl. No. 18/251,421 entitled "Systems and methods for improving ultrasound image quality," filed May 2, 2023.

Smith et al.; U.S. Appl. No. 18/344,278 entitled "Concave ultrasound transducers and 3d arrays," filed Jun. 29, 2023.

Call et al.; U.S. Appl. No. 18/344,479 entitled "Ultrasound imaging systems and methods for detecting object motion," filed Jun. 29, 2023.

Specht et al.; U.S. Appl. No. 18/588,967 entitled "Determining material stiffness using multiple aperaure ultrasound," filed Feb. 27, 2024.

Lockwood et al.; Real-time 3-D ultrasound imaging using sparse synthetic aperture beamforming; IEEE transactions on ultrasonics, ferroelectrics, and frequency control; 45(4); pp. 980-988; Jul. 1998.

* cited by examiner

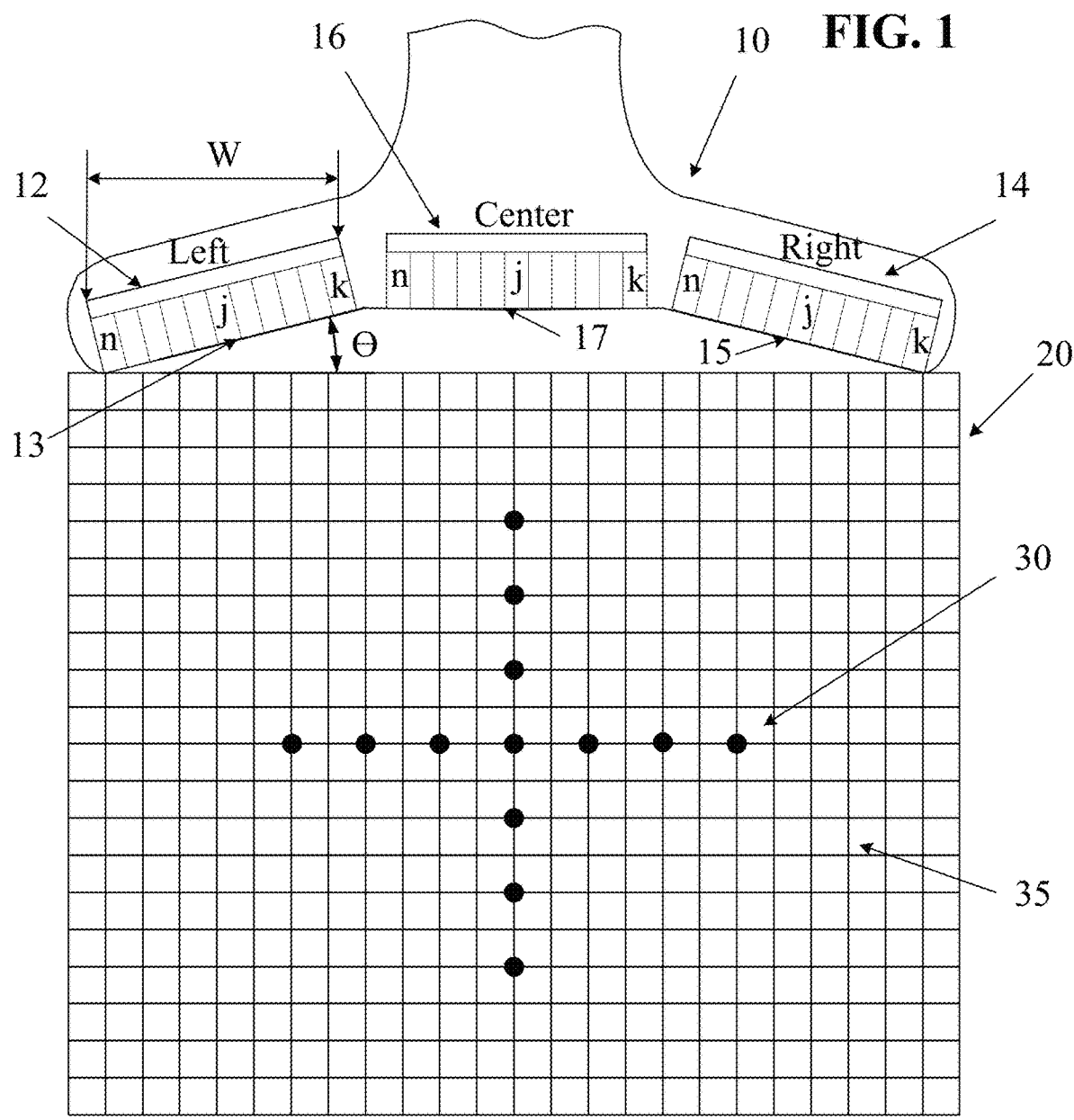
FIG. 1
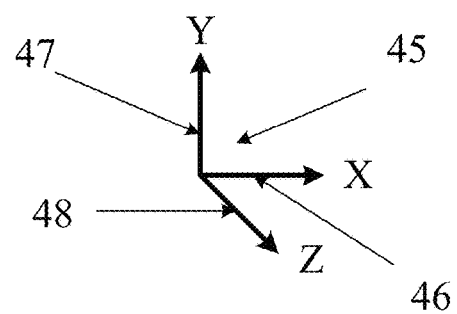

CALIBRATION OF MULTIPLE APERTURE ULTRASOUND PROBES

CROSS-REFERENCE TO RELATED APPLICATIONS

This application is a continuation of U.S. application Ser. No. 16/121,303, filed Sep. 4, 2018, now U.S. Pat. No. 11,253,233; which application is a continuation of U.S. application Ser. No. 15/400,826, filed Jan. 6, 2017, now U.S. Pat. No. 10,064,605; which application is a continuation of U.S. application Ser. No. 13/964,701, filed Aug. 12, 2013, now U.S. Pat. No. 9,572,549, which application claims the benefit of U.S. Provisional Application No. 61/681,986, filed Aug. 10, 2012, titled "Calibration of Multiple Aperture Ultrasound Probes", the contents of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to ultrasound imaging systems and more particularly to systems and methods for calibrating a multiple aperture ultrasound probe.

BACKGROUND

In conventional ultrasonic imaging, a focused beam of ultrasound energy is transmitted into body tissues to be examined and the returned echoes are detected and plotted to form an image. While ultrasound has been used extensively for diagnostic purposes, conventional ultrasound has been greatly limited by depth of scanning, speckle noise, poor lateral resolution, obscured tissues and other such problems.

In order to insonify body tissues, an ultrasound beam is typically formed and focused either by a phased array or a shaped transducer. Phased array ultrasound is a commonly used method of steering and focusing a narrow ultrasound beam for forming images in medical ultrasonography. A phased array probe has many small ultrasonic transducer elements, each of which can be pulsed individually. By varying the timing of ultrasound pulses (e.g., by pulsing elements one by one in sequence along a row), a pattern of constructive interference is set up that results in a beam directed at a chosen angle. This is known as beam steering. Such a steered ultrasound beam may then be swept through the tissue or object being examined. Data from multiple beams are then combined to make a visual image showing a slice through the object.

Traditionally, the same transducer or array used for transmitting an ultrasound beam is used to detect the returning echoes. This design configuration lies at the heart of one of the most significant limitations in the use of ultrasonic imaging for medical purposes: poor lateral resolution. Theoretically, the lateral resolution could be improved by increasing the width of the aperture of an ultrasonic probe, but practical problems involved with aperture size increase have kept apertures small. Unquestionably, ultrasonic imaging has been very useful even with this limitation, but it could be more effective with better resolution.

SUMMARY OF THE DISCLOSURE

A method of calibrating an ultrasound probe is provided, comprising the steps of placing a first array and a second array of the ultrasound probe in position to image a phantom, each of the first and second arrays having a plurality of transducer elements, imaging the phantom with the first array to obtain a reference image, wherein imaging is dependent on data describing a position of each transducer element of the first array, imaging the phantom with the second array to obtain a test image, wherein imaging is dependent on data describing a position of each transducer element of the second array, quantifying a first error between the reference image and the test image; iteratively optimizing the data describing the position of each transducer element of the second array until the first error is at a minimum.

In some embodiments, the method further comprises imaging the phantom with a third array of the ultrasound probe to obtain a second test image, the third array having a plurality of transducer elements, quantifying a second error between the reference image and the second test image and iteratively optimizing data describing a position of each element of the third array until the second error is minimized.

In some embodiments, the method further comprises storing raw echo data received while imaging the phantom with the second array.

In one embodiment, the iteratively optimizing step comprises adjusting the data describing the position of the transducer elements of the second array to create first adjusted position data, re-beamforming the stored echo data using the first adjusted position data to form a second test image of the reflectors, quantifying a second error between the second test image and the reference image, and determining whether the second error is less than the first error.

In one embodiment, adjusting the data describing the position of the transducer elements of the second array includes adjusting a position of a reference point of the array and an angle of a surface of the array, but does not include adjusting a spacing between the elements of the second array.

In some embodiments, the method further comprises, after a first iteratively optimizing step, performing a second iteratively optimizing step comprising adjusting the first adjusted position data, including adjusting a spacing between at least two transducer elements of the second array to create second adjusted position data, re-beamforming the stored echo data using the second adjusted position data to form a third test image of the reflectors, quantifying a third error between the third test image and the reference image, and determining whether the third error is less than the second error.

In one embodiment, iteratively optimizing the transducer element position data comprises optimizing using a least squares optimization process.

In other embodiments, quantifying the first error comprises quantifying a distance between positions of reflectors in the reference image relative to positions of the same reflectors in the test image. In some embodiments, quantifying the first error comprises quantifying a difference in brightness between reflectors in the reference image and reflectors in the test image. In additional embodiments, quantifying the first error comprises quantifying a difference between a pattern of reflectors and holes in the reference image compared with a pattern of holes and reflectors in the test image.

In one embodiment, the reference image and the test image are three-dimensional volumetric images of a three-dimensional pattern of reflectors, holes, or both reflectors and holes.

In other embodiments, wherein the phantom comprises living tissue.

In some embodiments, the method further comprises identifying positions of reflectors in the phantom and fitting a mathematically defined curve to a detected pattern of reflectors.

In one embodiment, the curve is a straight line.

In other embodiments, the step of quantifying a first error comprises calculating a coefficient of determination that quantifies a degree of fit of the curve to the pattern of reflectors.

A method of calibrating an ultrasound probe is provided, comprising the steps of insonifying a plurality of reflectors of a phantom with the ultrasound probe, receiving echo data with the ultrasound probe, storing the echo data, beamforming the stored echo data using first transducer element position data to form an image of the reflectors, obtaining reference data describing the reflectors, quantifying an error between the image and the reference data, and iteratively optimizing the transducer element position data based on the quantified error.

In some embodiments, the iteratively optimizing step comprises iteratively optimizing the transducer element position data with a least squares optimization process.

In one embodiment, the iteratively optimizing step comprises adjusting the transducer element position data, re-beamforming the stored echo data using the adjusted transducer element position data to form a second image of the reflectors, quantifying a second error based on the second image, and evaluating the second error to determine whether the adjusted transducer element position data improves the image.

In some embodiments, adjusting the transducer element position data comprises adjusting an array horizontal position variable, an array vertical position variable and an array angle variable. In other embodiments, adjusting the transducer element position data does not comprise adjusting a spacing between adjacent transducer elements on a common array.

In one embodiment, the reference data is based on physical measurements of the phantom.

In some embodiments, the method further comprises deriving the reference data from a reference image of the phantom.

In one embodiment, the reference image is obtained using a different group of transducer elements of the probe than a group of transducer elements used for the insonifying and receiving steps.

In additional embodiments, the step of iteratively optimizing the transducer element position data comprises using a least squares optimization process.

In some embodiments, the method further comprises identifying positions of reflectors in the phantom and fitting a mathematically defined curve to a detected pattern of reflectors. In one embodiment, the curve is a straight line.

In some embodiments, the step of quantifying a first error comprises calculating a coefficient of determination that quantifies a degree of fit of the curve to the pattern of reflectors.

A method of calibrating ultrasound imaging data is also provided, comprising the steps of retrieving raw echo data from a memory device, the raw echo data comprising a plurality of echo strings, each echo string comprising a collection of echo records corresponding to echoes of a single ultrasound ping transmitted from a single transmit aperture and received by a single receive element, retrieving first calibration data describing a position of each receive transducer element corresponding to each echo string, retrieving second calibration data describing a position of at least one transducer element corresponding to a transmitted ping associated with each echo string, forming a reference image by beamforming a first collection of echo strings corresponding to a first group of receive transducer elements, wherein beamforming comprises triangulating a position of reflectors based on the first and second calibration data, forming a test image by beamforming a second collection of echo strings corresponding to a second group of transducer elements that is not identical to the first group of transducer elements, quantifying first error between the reference image and the test image, adjusting first calibration data to describe adjusted positions for the elements of the second group, re-beamforming the test image with the adjusted positions for the elements of the second group to obtain a second test image, quantifying a second error between the second test image and the reference image, and evaluating the new error to determine whether the second error is less than the first error.

In some embodiments, the method is performed without any physical or electronic connection to a probe used to create the raw echo data.

In some embodiments, there is no ultrasound probe connected to the memory device.

An ultrasound probe calibration system is provided, comprising an ultrasound probe having a plurality of transmit transducer elements and a plurality of receive transducer elements, a phantom having a pattern of reflectors, a first memory device containing reference data describing the pattern of reflectors of the phantom, a second memory device containing transducer element position data describing a position of each transmit transducer element and each receive transducer element relative to a common coordinate system, and an imaging control system containing calibration program code configured to direct the system to insonify the phantom with the transmit transducer elements, receive echo data with the receive transducer elements, and store echo data in a third memory device, form a first image of the pattern of reflectors by beamforming the stored echo data using the transducer element position data, determine measurement data describing a position of the pattern of reflectors as indicated by the first image, quantify an error between the measurement data and the reference data, and iteratively optimize the transducer element position data based on the quantified error.

In some embodiments, the imaging control system is configured to iteratively optimize the phantom by adjusting the transducer element position data; forming a second image of the pattern of reflectors by re-beamforming the stored echo data using the adjusted transducer element position data quantifying a second error based on the second image and evaluating the second error to determine whether the adjusted transducer element position data improves the image.

In one embodiment, the reference data is based on physical measurements of the phantom.

In other embodiments, the reference data is based on a reference image.

In some embodiments, the imaging control system is configured to iteratively optimize the transducer element position data using a least squares optimization process.

In other embodiments, the phantom further comprises at least one region that absorbs ultrasound signals.

In some embodiments, the ultrasound probe comprises a plurality of transducer arrays. In another embodiment, the ultrasound probe comprises a single continuous transducer array. In one embodiment, the ultrasound probe comprises a transducer array with a concave curvature.

In some embodiments, the phantom comprises a pattern of pins.

In one embodiment, the phantom comprises living tissue.

In some embodiments, the calibration program code is configured to determine measurement data by fitting a curve to a detected pattern of reflectors.

In one embodiment, the calibration program code is configured to quantify an error by determining a coefficient of determination quantifying a degree of fit of the curve.

In another embodiment, at least two of the first memory device, the second memory device, and the third memory device are logical portions of a single physical memory device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 is a schematic illustration of an embodiment of a three-aperture ultrasound imaging probe and a phantom object being imaged.

DETAILED DESCRIPTION

Figure 2:
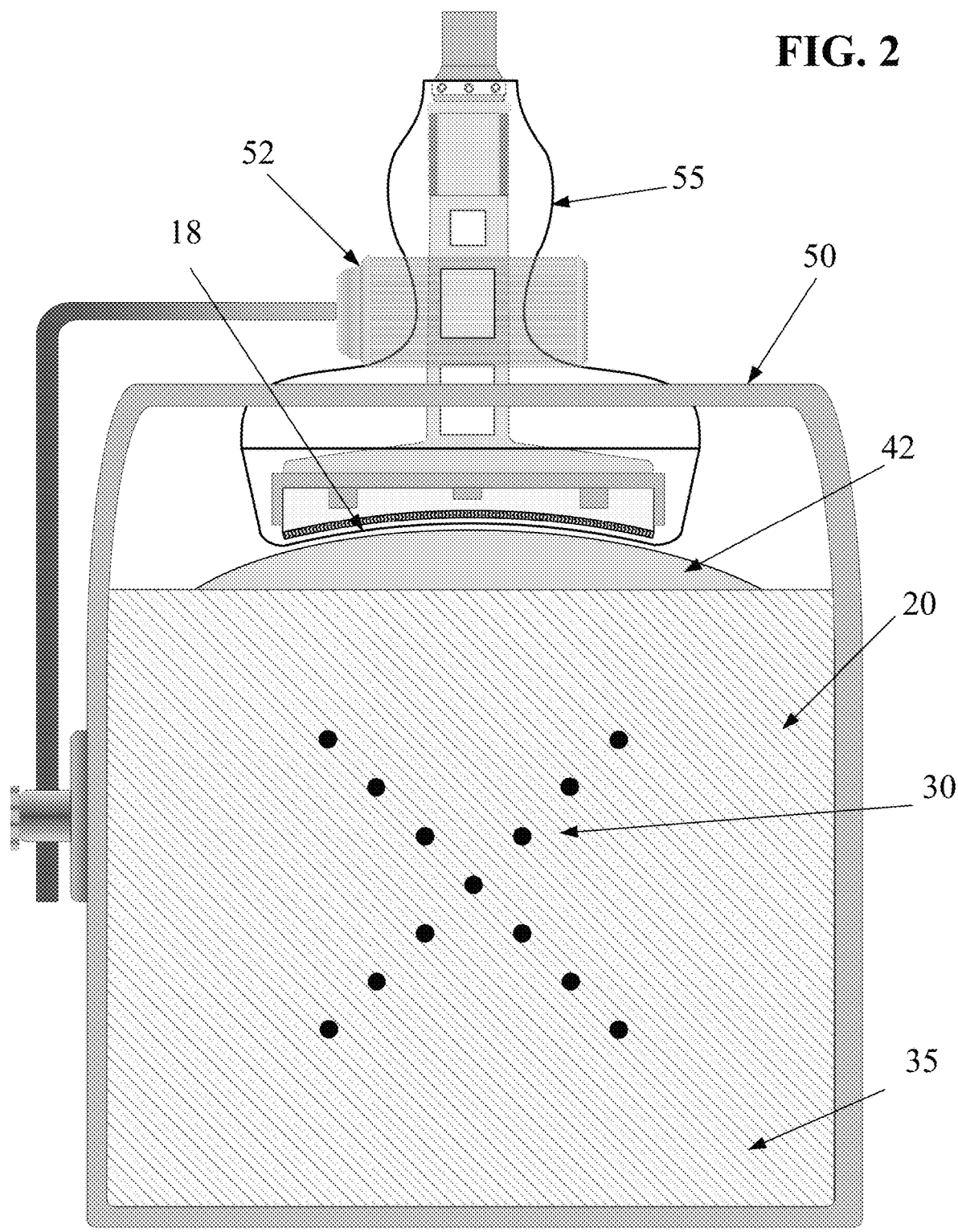
FIG. 2 is a section view of one embodiment of a multiple aperture ultrasound probe with a continuous curvilinear array positioned above a phantom and held in place by a clamp mechanism.

The various embodiments will be described in detail with reference to the accompanying drawings. References made to particular examples and implementations are for illustrative purposes, and are not intended to limit the scope of the invention or the claims.

The various embodiments herein provide systems and methods for dynamically calibrating a multiple aperture ultrasound probe using a static phantom. Calibration of a multiple aperture ultrasound imaging probe may generally comprise determining an acoustic position of each transducer element in the probe. Some embodiments of a dynamic calibration process may generally include the steps of imaging a calibration phantom having a known pattern of reflectors, quantifying an error between known information about the phantom and information obtained from the imaging, and performing an iterative optimization routine to minimize an error function in order to obtain improved transducer element position variables. Such improved transducer element position variables may then be stored for use during subsequent imaging using the calibrated probe.

Introduction & Definitions

Although the various embodiments are described herein with reference to ultrasound imaging of various anatomic structures, it will be understood that many of the methods and devices shown and described herein may also be used in other applications, such as imaging and evaluating non-anatomic structures and objects. For example, the probes, systems and methods described herein may be used in non-destructive testing or evaluation of various mechanical objects, structural objects or materials, such as welds, pipes, beams, plates, pressure vessels, etc.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In other embodiments, ultrasound transducers may comprise capacitive micromachined ultrasound transducers (CMUT).

Transducers are often configured in arrays of multiple individual transducer elements. As used herein, the terms "transducer array" or "array" generally refers to a collection of transducer elements mounted to a common backing plate. Such arrays may have one dimension (1D), two dimensions (2D), 1.X dimensions (1.XD) or three dimensions (3D). Other dimensioned arrays as understood by those skilled in the art may also be used. Annular arrays, such as concentric circular arrays and elliptical arrays may also be used. An element of a transducer array may be the smallest discretely functional component of an array. For example, in the case of an array of piezoelectric transducer elements, each element may be a single piezoelectric crystal or a single machined section of a piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein, the term "aperture" may refer to a conceptual "opening" through which ultrasound signals may be sent and/or received. In actual practice, an aperture is simply a single transducer element or a group of transducer elements that are collectively managed as a common group by imaging control electronics. For example, in some embodiments an aperture may be a physical grouping of elements which may be physically separated from elements of an adjacent aperture. However, adjacent apertures need not necessarily be physically separated.

It should be noted that the terms "receive aperture," "insonifying aperture," and/or "transmit aperture" are used herein to mean an individual element, a group of elements within an array, or even entire arrays with in a common housing, that perform the desired transmit or receive function from a desired physical viewpoint or aperture. In some embodiments, such transmit and receive apertures may be created as physically separate components with dedicated functionality. In other embodiments, any number of send and/or receive apertures may be dynamically defined electronically as needed. In other embodiments, a multiple aperture ultrasound imaging system may use a combination of dedicated-function and dynamic-function apertures.

As used herein, the term "total aperture" refers to the total cumulative size of all imaging apertures. In other words, the term "total aperture" may refer to one or more dimensions defined by a maximum distance between the furthest-most transducer elements of any combination of send and/or receive elements used for a particular imaging cycle. Thus, the total aperture is made up of any number of sub-apertures designated as send or receive apertures for a particular cycle. In the case of a single-aperture imaging arrangement, the total aperture, sub-aperture, transmit aperture, and receive aperture will all have the same dimensions. In the case of a multiple array probe, the dimensions of the total aperture may include the sum of the dimensions of all of the arrays.

In some embodiments, two apertures may be located adjacent one another on a continuous array. In still other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below and/or will be clear to the skilled artisan.

Elements and arrays described herein may also be multi-function. That is, the designation of transducer elements or arrays as transmitters in one instance does not preclude their immediate redesignation as receivers in the next instance. Moreover, embodiments of the control system herein include the capabilities for making such designations electronically based on user inputs, pre-set scan or resolution criteria, or other automatically determined criteria.

As used herein the term "point source transmission" may refer to an introduction of transmitted ultrasound energy into a medium from single spatial location. This may be accomplished using a single ultrasound transducer element or combination of adjacent transducer elements transmitting together as a single transmit aperture. A single transmission from a point source transmit aperture approximates a uniform spherical wave front, or in the case of imaging a 2D slice, a uniform circular wave front within the 2D slice. In some cases, a single transmission of a circular or spherical wave front from a point source transmit aperture may be referred to herein as a "ping" or a "point source pulse."

Point source transmission differs in its spatial characteristics from a "phased array transmission" which focuses energy in a particular direction from the transducer element array. Phased array transmission manipulates the phase of a group of transducer elements in sequence so as to strengthen or steer an insonifying wave to a specific region of interest. A short duration phased array transmission may be referred to herein as a "phased array pulse."

In some embodiments, multiple aperture imaging using a series of transmitted pings may operate by transmitting a point-source ping from a first transmit aperture and receiving echoes with elements of two or more receive apertures, one or more of which may include some or all elements of a transmit aperture. A complete image may be formed by triangulating the position of scatterers based on delay times between ping transmission and reception of echoes, the speed of sound, and the relative positions of transmit and receive transducer elements. As a result, each receive aperture may form a complete image from echoes of each transmitted ping. In some embodiments, a single time domain frame may be formed by combining images formed from echoes at two or more receive apertures from a single transmitted ping. In other embodiments, a single time domain frame may be formed by combining images formed from echoes received at one or more receive apertures from two or more transmitted pings. In some such embodiments, the multiple transmitted pings may originate from different transmit apertures.

FIG. 1 illustrates an embodiment of a three-array multiple aperture ultrasound imaging probe 10 and a phantom 20 to be imaged. The phantom 20 generally includes a pattern of reflectors 30 within a solid or liquid medium 35. In some embodiments, a phantom 20 may also include one or more "holes"—regions or objects that substantially absorb and do not reflect significant ultrasound signals. The probe 10 is shown with a left transducer array 12 which may include three transmit apertures labeled 'n,' 'j,' and 'k' (which may be referred to herein by short-hand designations Ln, Lj and Lk). A right transducer array 14 may also include three transmit apertures 'n,' 'j,' and 'k' (which may be referred to herein by short-hand designations Rn, Rj and Rk). Some or all of the elements of the left transducer array 12 may also be designated as a left receive aperture 13. Similarly, some or all of the elements of the right transducer array 14 may be designated as a right receive aperture 15. In addition to the left and right arrays, a multiple aperture ultrasound probe 10 may include a center transducer array 16, which may include three transmit apertures labeled 'n,' 'j,' and 'k' (which may be referred to herein by short-hand designations Cn, Cj and Ck). Some or all of the elements of the center transducer array 16 may also be designated as a center receive aperture 17. It should be understood that each of the three apertures can include any number of transducer elements which may be spaced from one another in one, two or three dimensions.

Figure 3:
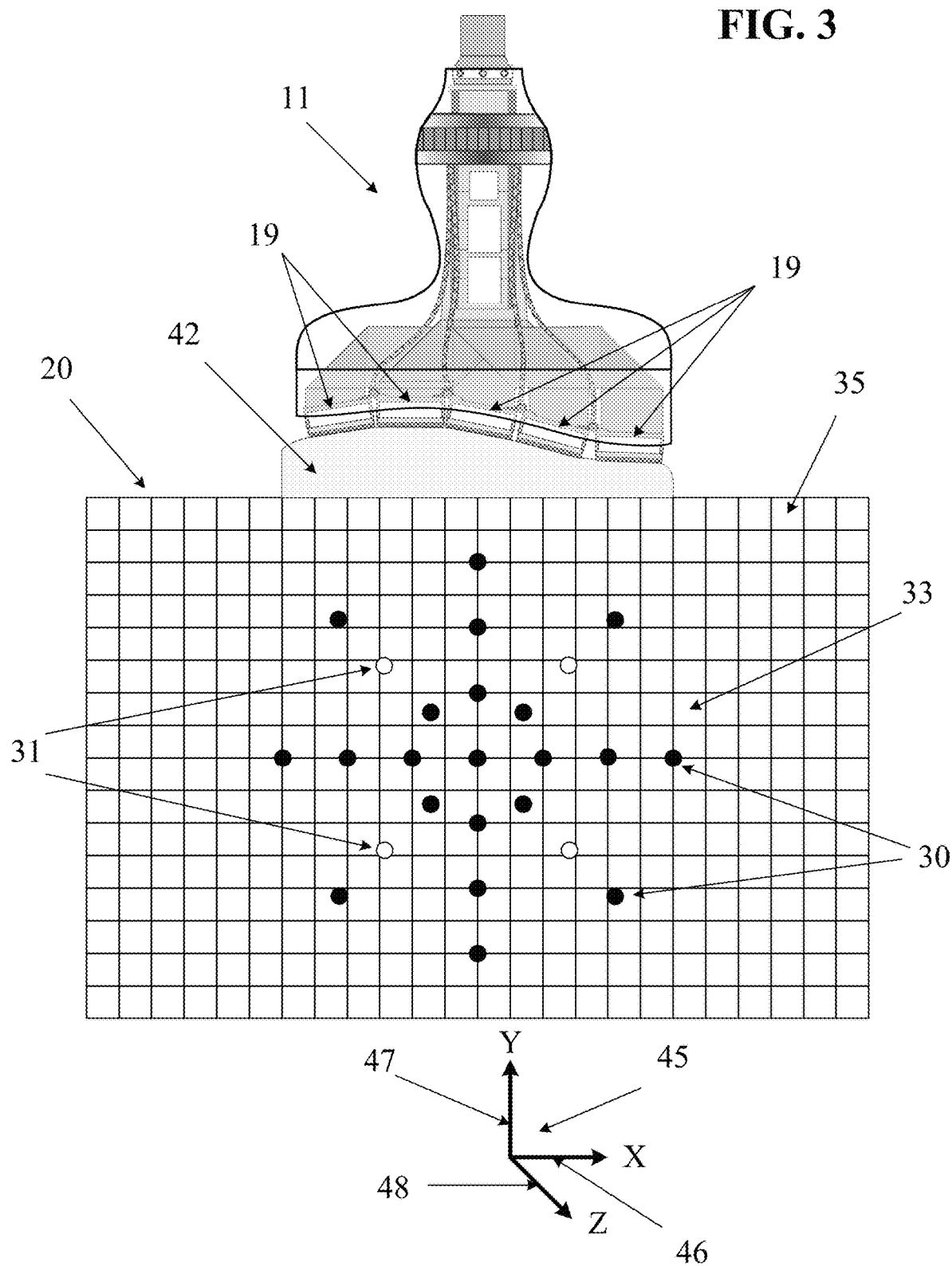
FIG. 3 is a section view of an embodiment of an adjustable multiple aperture imaging probe positioned above a phantom.
Figure 4A:
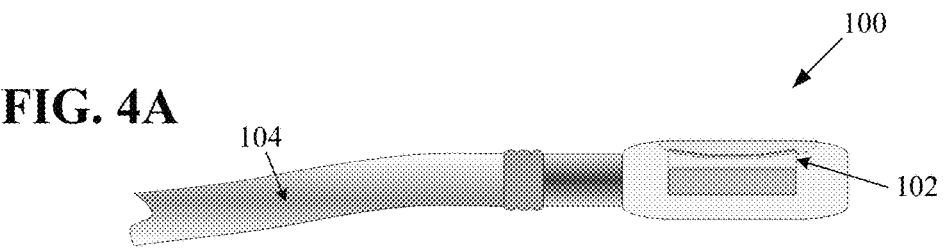
FIG. 4A is a longitudinal sectional view of a multiple aperture ultrasound imaging probe configured for transesophageal ultrasound imaging.
Figure 4B:
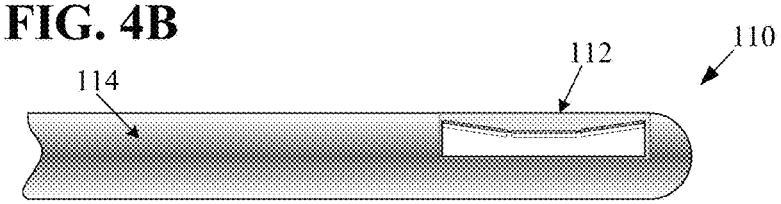
FIG. 4B is a longitudinal sectional view of a multiple aperture ultrasound imaging probe configured for transrectal ultrasound imaging.
Figure 4C:
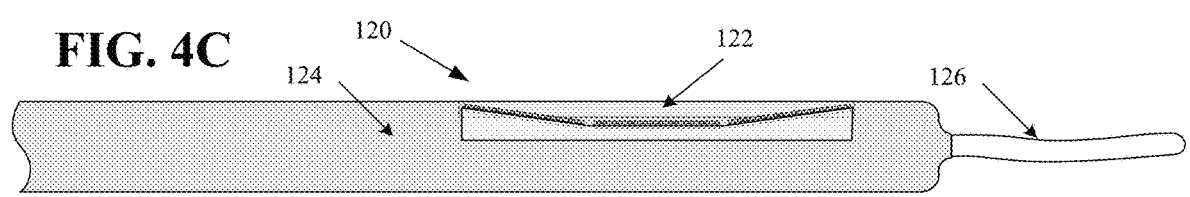
FIG. 4C is a longitudinal sectional view of a multiple aperture ultrasound imaging probe configured for intravenous ultrasound.
Figure 4D:
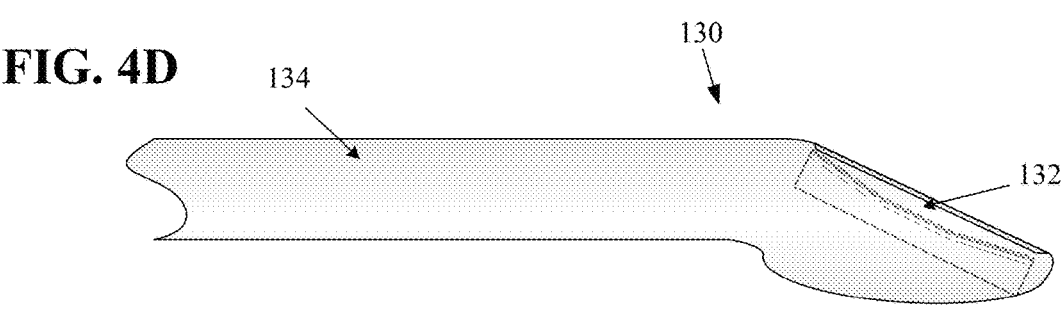
FIG. 4D is a longitudinal sectional view of a multiple aperture ultrasound imaging probe configured for transvaginal ultrasound imaging.
Figure 4E:
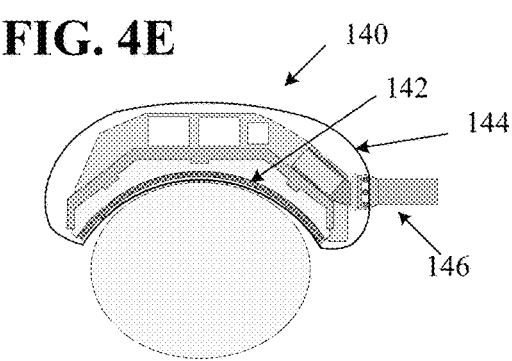
FIG. 4E is a sectional view of a multiple aperture ultrasound imaging probe configured for imaging round structures or features.
Figure 4F:
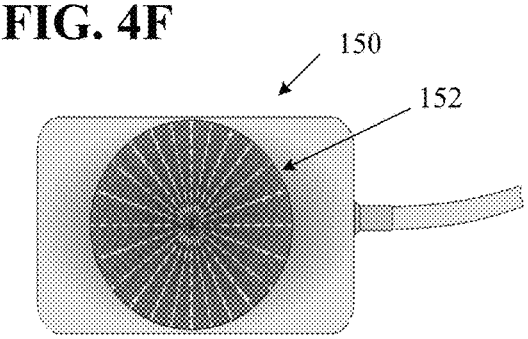
FIG. 4F is a plan view of a multiple aperture ultrasound imaging probe with a radial array of transducer elements configured for three-dimensional imaging.

In other embodiments, any other multiple aperture ultrasound imaging probe may be calibrated using the systems and methods described below. For example, FIG. 2 illustrates a multiple aperture ultrasound probe 55 with a single large (i.e., larger than an expected coherence width for an intended imaging application) continuous curved array 18 positioned over a phantom 20. Some embodiments of the calibration methods and devices below may be particularly useful with adjustable probes such as that illustrated in FIG. 3. FIG. 3 illustrates an adjustable multiple aperture ultrasound probe 11 positioned over a phantom 20. FIG. 4A illustrates a multiple aperture ultrasound probe 100 with one or more transducer arrays 102 positioned at a distal end of an endoscope 104 sized and configured for transesophageal positioning and imaging. FIG. 4B illustrates a multiple aperture ultrasound probe 110 with one or more transducer arrays 112 and a housing 114 sized and configured for trans-rectal positioning and imaging. FIG. 4C illustrates a multiple aperture ultrasound probe 120 including one or more transducer arrays 122 and a housing 124 positioned at a distal end of a catheter 126 all of which may be sized and configured for intravenous positioning and imaging. FIG. 4D illustrates a multiple aperture ultrasound probe 130 with one or more transducer arrays 132 and a housing 134 sized and configured for trans-vaginal positioning and imaging. FIG. 4E illustrates a multiple aperture ultrasound probe 140 with a continuous curved transducer array 142 and a housing 144 and a side-mounted cable 146 sized and configured for positioning over curved anatomical structures such as arms and legs. FIG. 4F illustrates a multiple aperture ultrasound probe 150 with a large circular array 152 that may have a concave curvature about two axes. The probe of FIG. 4F and other probes may include transducer elements with substantial displacement along orthogonal axes. Such probes may be particularly suitable for directly obtaining echo data from a three-dimensional volume. Any of these or other ultrasound probes (including single-aperture ultrasound probes) may be calibrated using the systems and methods herein.

As used herein, the term "phantom" may refer to any substantially static object to be imaged by an ultrasound probe. For example, any number of phantoms designed for sonographer training are widely commercially available from various suppliers of medical equipment, such as Gammex, Inc. (gammex.com). Some commercially available phantoms are made to mimic the imaging characteristics of objects to be imaged such as specific or generic human tissues. Such properties may or may not be required by various embodiments of the invention as will be further described below. The term "phantom" may also include other objects with substantially static reflectors, such as a region of a human or animal body with substantially static strong reflectors. An object need not be purpose-built as a phantom to be used as a phantom for the calibration processes described herein.

With reference to FIG. 1, in one example embodiment of a multiple aperture imaging process, a first image may be formed by transmitting a first ping from a first transmit aperture Ln and receiving echoes of the first ping at a left receive aperture 13. A second image may be formed from echoes of the first ping received at the right receive aperture 15. Third and fourth images may be formed by transmitting a second ping from a second transmit aperture Lj and receiving echoes of the second ping at the left receive aperture 13 and the right receive aperture 15. In some embodiments, all four images may then be combined to form a single time domain frame. In other embodiments, a single time domain frame may be obtained from echoes received at any number of receive apertures from any number of pings transmitted by any number of transmit apertures. Time domain frames may then be displayed sequentially on a display screen as a continuous moving image. Still images may also be formed using any of the above techniques.

In some embodiments, the width of a receive aperture may be limited by the assumption that the speed of sound is the same for every path from a scatterer to each element of the receive aperture. In a narrow enough receive aperture this simplifying assumption is acceptable. However, as receive aperture width increases, an inflection point is reached (referred to herein as the "maximum coherent aperture width" or "coherence width") at which the echo return paths will necessarily pass though different types of tissue having different speeds of sound. When this difference results in phase shifts in excess of 180 degrees, additional receive elements beyond the maximum coherent receive aperture width will actually degrade the image rather than improve it. The coherence width will vary depending on an intended imaging application and is difficult if not impossible to predict in advance.

Therefore, in order to make use of a wide probe with a total aperture width greater than the maximum coherent width, the full probe width may be physically or logically divided into multiple apertures, each of which may be limited to a width less than the maximum coherent aperture width and small enough to avoid phase cancellation of received signals. The maximum coherent width can be different for different patients and for different probe positions on the same patient. In some embodiments, a compromise width may be determined for a given probe system. In other embodiments, a multiple aperture ultrasound imaging control system may be configured with a dynamic algorithm to subdivide the available elements in multiple apertures into groups that are small enough to avoid significant phase cancellation.

In some embodiments, it may be difficult or impossible to meet additional design constraints while grouping elements into apertures with a width less than the maximum coherent width. For example, if material is too heterogeneous over very small areas, it may be impractical to form apertures small enough to be less than the maximum coherent width. Similarly, if a system is designed to image a very small target at a substantial depth, an aperture with a width greater than the maximum coherent width may be needed. In such cases, a receive aperture with a width greater than the maximum coherent width can be accommodated by making additional adjustments or corrections may be made to account for differences in the speed-of-sound along different paths. Some examples of such speed-of-sound adjustments are provided herein.

With a multiple aperture probe using a point-source transmission imaging technique (also referred to as ping-based imaging), each image pixel may be assembled by beamforming received echo data to combine information from echoes received at each of the multiple receive apertures and from each of the multiple transmit apertures. In some embodiments of multiple aperture imaging with point-source transmission, receive beamforming comprises forming a pixel of a reconstructed image by summing time-delayed echo returns on receive transducer elements from a scatterer in the object being examined. The time delays may be determined by the geometry of the probe elements and an assumed value for the speed of sound through the medium being imaged.

The locus of a single reflector will lie along an ellipse with a first focus at the position of the transmit transducer element(s) and the second focus at the position of the receive transducer element. Although several other possible reflectors lie along the same ellipse, echoes of the same reflector will also be received by each of the other receive transducer elements of a receive aperture. The slightly different positions of each receive transducer element means that each receive element will define a slightly different ellipse for a given reflector. Accumulating the results by coherently summing the ellipses for all elements of a common receive aperture will indicate an intersection of the ellipses for a reflector, thereby converging towards a point at which to display a pixel representing the reflector. The echo amplitudes received by any number of receive elements may thereby be combined into each pixel value. In other embodiments the computation can be organized differently to arrive at substantially the same image.

Because the position of each transmit and receive element plays an important role in producing an image during ping-based ultrasound imaging, the quality of an image produced from ping-based imaging is substantially dependent on the accuracy of the information describing the relative positions of the transducer elements.

Various algorithms may be used for combining echo signals received by separate receive elements. For example, some embodiments may process echo-signals individually, plotting each echo signal at all possible locations along its ellipse, then proceeding to the next echo signal. Alternatively, each pixel location may be processed individually, identifying and processing all echoes potentially contributing to that pixel location before proceeding to the next pixel location.

Image quality may be further improved by combining images formed by the beamformer from one or more subsequent transmitted pings, transmitted from the same or a different point source (or multiple different point sources). Still further improvements to image quality may be obtained by combining images formed by more than one receive aperture. An important consideration is whether the summation of images from different pings, different transmit point-sources or different receive apertures should be coherent summation (phase sensitive) or incoherent summation (summing magnitude of the signals without phase information).

In some embodiments, multiple aperture imaging using a series of transmitted pings may operate by transmitting a point-source ping from a first transmit aperture and receiving echoes with elements of one or more receive apertures (which may overlap with the transmit aperture). A complete image may be formed by triangulating the position of scatterers based on delay times between transmission and receiving echoes and the known position of each receive element relative to each point-source transmit aperture. As a result, a complete image may be formed from data received at each receive aperture from echoes of each transmitted ping.

Images obtained from different unique combinations of a ping and a receive aperture may be referred to herein as image layers. Multiple image layers may be combined to improve the overall quality of a final combined image. Thus, in some embodiments, the number of image layers can be the product of the number of receive apertures and the number of transmit apertures (where a "transmit aperture" can be a single transmit element or a group of transmit elements). In other embodiments, the same ping imaging processes may also be performed using a single receive aperture.

Phantom Calibration Embodiments

Some embodiments of ultrasound probe calibration methods using a phantom may generally include the steps of characterizing the phantom using some known baseline reference data, then imaging the phantom with the probe to be calibrated. An error between the known reference data and data obtained from the generated image may then be quantified and an iterative optimization routine may be used to obtain improved transducer element position information. Such improved transducer element position variables may then be stored for use during subsequent imaging using the calibrated probe.

FIG. 1 illustrates one embodiment of a phantom 20 that may be used for calibrating a multiple aperture probe. In some embodiments, a phantom 20 for calibrating a multiple aperture probe may include a plurality of reflectors 30 arranged in a two-dimensional pattern within a solid, liquid or gel material 35 that has a consistent and known speed-of-sound. The reflectors may be made of any material, such as a plastic, metal, wood, ceramic, or any other solid material that is substantially highly reflective of ultrasound waves relative to the surrounding medium.

In some embodiments, reflectors 30 may be arranged in the phantom 20 in a pattern that may have characteristics selected to facilitate a calibration process. For example, a non-repeating reflector pattern will allow a calibration process to recognize an imaged position of the reflectors without confusion. For example, a complete grid pattern is highly repetitive because portions of the pattern are identically duplicated merely by shifting one full grid position. In some embodiments, the pattern of reflectors may also comprise a number of reflectors with displacement along the X axis 46 that is approximately equal to a number of reflectors with displacement along the Y axis 47. Thus, in some embodiments a pattern in the shape of a cross or a plus sign may be used. In other embodiments, reflectors may be positioned randomly or in other patterns, such as an X-shape, an asterisk, a sunburst, a spiral or any other pattern.

In some embodiments, reflectors may also have depth or distinguishable detail in the z-direction 48. For example, the reflectors 30 may be rods with longitudinal axes along the z-direction 48. Alternatively, the reflectors may be substantially spherical or uniform three-dimensional shapes. In other embodiments, an arrangement of intersecting wires or rods may be used to form a distinguishable pattern in three-dimensional space within a phantom.

The reflectors 30 in the calibration phantom 20 may be of any size or shape as desired. In some embodiments, the reflectors 30 may have a circular diameter that is on the same order of magnitude as the wavelength of the ultrasound signals being used. In general, smaller reflectors may provide better calibration, but in some embodiments the precise size of the reflectors need not be an important factor. In some embodiments, all reflectors 30 in the phantom may be the same size as one another, while in other embodiments, reflectors 30 may be provided in a variety of sizes.

In some embodiments, the physical size and location of the reflectors in the phantom 20 may be determined by mechanical measurement of the phantom (or by other methods, such as optical measurement or ultrasonic measurement using a known-calibrated system) prior to, during or after construction of the phantom. Reflector position reference data may then by obtained by storing the reflector location information within a memory device accessible by software or firmware performing a calibration process. Such reference data may include information such as the position, size, orientation, arrangement or other information about the reflectors and/or holes in the phantom. Reference data may be represented or stored as a reference image or as a series of data points. Alternatively, reference data may be extracted from a reference ultrasound image.

In some embodiments, a reference image of the phantom may be obtained using a probe or an array within a probe that is known to be well-calibrated. In other embodiments, a reference image of the phantom may be obtained using a selected group of elements of the probe. Reflector size and/or location information may then be determined from the reference image for use in calibrating remaining elements of the probe or a different probe.

Therefore, in some embodiments a reference image may be obtained by retrieving previously-determined reflector position data from a memory device. In other embodiments, a reference image may be obtained by imaging the phantom using a sub-set of all elements in a probe. In some embodiments, it may be desirable to obtain a reference image using an aperture that is no wider than an assumed maximum coherence width (as described above). This allows for a reference image to be formed without the need to correct for speed-of-sound variations along different ultrasound wave paths. If the phantom is known to have a uniform speed-of-sound (except for reflectors and/or holes), then the coherence width may be as large as an entire total aperture of a multiple aperture probe. In such embodiments, obtaining a reference image with a receive aperture smaller than the coherence width for an intended imaging application may be useful as a starting point.

For example, when calibrating a three-array probe such as that shown in FIG. 1, a reference image may be obtained by imaging the phantom 20 using only one of the arrays (e.g., the center array 16, the left array 12 or the right array 14). In other embodiments, such as when calibrating a probe with a continuous convex transducer array 19 such as that shown in FIG. 2, a reference image may be obtained by imaging the phantom 20 using only a small group of transducer elements of the array. For example, a group of elements near the center of the curved array may be used as transmit and/or receive elements for obtaining a reference image. Similarly, a reference image may be obtained using a single adjustable array 19 of an adjustable probe 11 such as that shown in FIG. 3. Reference images may be obtained using any multiple aperture ultrasound imaging probe in a similar manner.

As shown for example in FIG. 2, in some embodiments the phantom may be mounted in an enclosure that includes a probe-retaining portion 50. A mounting bracket 52 may also be provided to securely hold the probe 55 in a consistent position relative to the phantom 20 during a calibration process. Any mechanical bracket may be used. In some embodiments, a coupling gel and/or a gel or fluid-filled standoff 42 may be used to provide a continuous medium through which the ultrasound signals will pass. The coupling gel and/or standoff 42 should have approximately the same speed-of-sound as the phantom medium. In some embodiments, a standoff 42 may be a liquid or gel-filled bag.

Figure 5A:
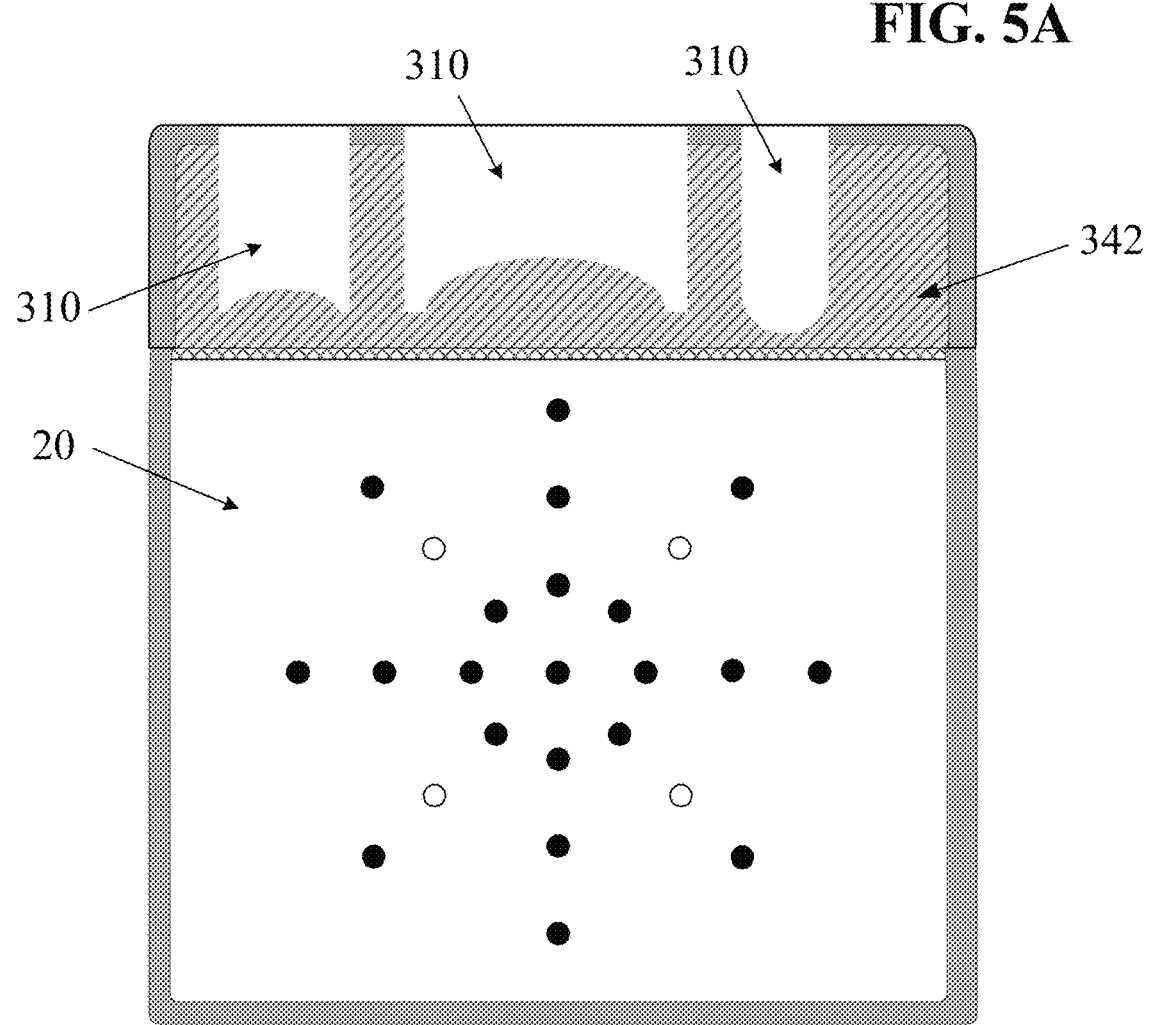
FIG. 5A is a cross-sectional view of an ultrasound probe calibration phantom having a docking section with receiving slots for receiving and retaining ultrasound probes to be calibrated.
Figure 5B:
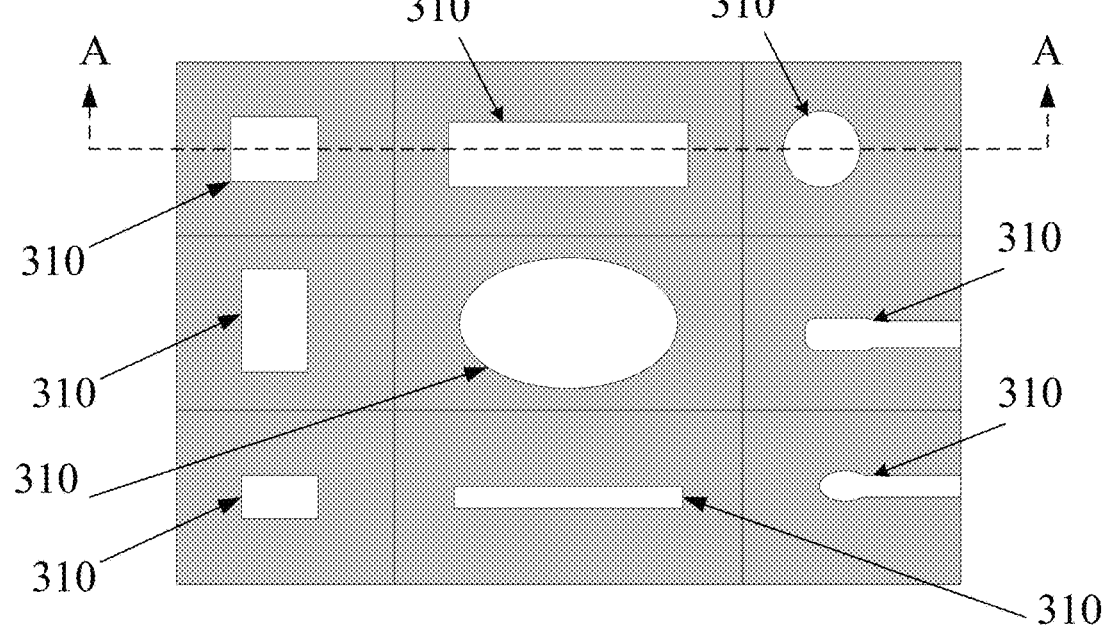
FIG. 5B is a top plan view of the ultrasound probe calibration phantom docking section of FIG. 5A.

FIG. 5A illustrates an alternative arrangement comprising a docking section 342 having a plurality of receiving slots 310 designed to receive probes of specific shapes. The docking section 342 may be made of the same material as the material of the phantom 20. Alternatively, the docking section 342 may be made of a material having the same speed-of-sound characteristics as the phantom 20. As shown in FIG. 5B, many probe receiving slots 310 may be provided for a single docking section 342. In various embodiments, each probe receiving slot 310 may be sized, shaped, and otherwise configured to receive one or more specific ultrasound probes.

Figure 6:
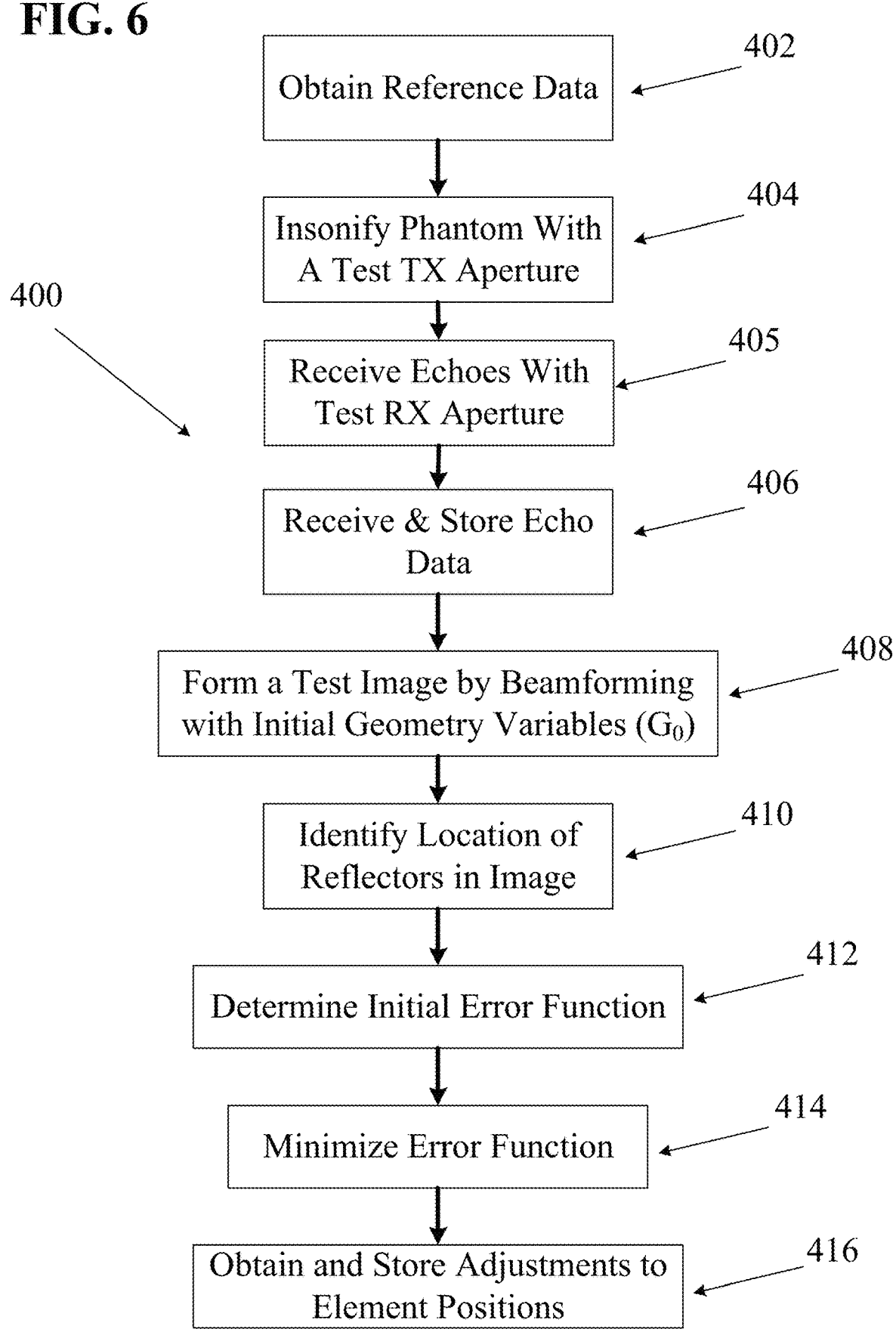
FIG. 6 is a process flow diagram of one embodiment of a process for calibrating a multiple aperture ultrasound probe using a static phantom.

FIG. 6 is a process flow diagram illustrating an embodiment of a process 400 for calibrating a multiple aperture probe using a phantom. In general, some embodiments of the process 400 may comprise the steps of obtaining reference data 402 that characterizes known information about the phantom (such as reflector or hole positions, sizes, etc.), insonifying the phantom with a test transmit (TX) aperture 404, receiving echoes with a test receive (RX) aperture 405, at least temporarily storing the received echo data 406, forming a test image of the reflectors by beamforming the echo data 408, determining an error function 412 based on a comparison of the generated image and the reference data, and minimizing the error function 414 to obtain improved transducer element position variables 416. The resulting improved element position information may be stored in a memory device for subsequent use by a beamforming process. Steps 404-416 may then be repeated for each additional transmit and/or aperture in the probe, and the position of each transducer element in each transmit and/or receive aperture within the probe may be determined relative to a common coordinate system.

In some embodiments, the process 400 may be entirely automated in software or firmware. In other embodiments, at least some steps may involve human participation, such as to identify or to quantify an error between an obtained image and a reference image. In other embodiments, a human user may also be called upon to determine whether a resulting image is "good enough" or whether the calibration process should be repeated or continued.

In various embodiments, the process 400 may be used to calibrate the position of one or more test transmit apertures, one or more test receive apertures, or both. The choice of which type of aperture to calibrate may depend on factors such as the construction of the probe, the number of transmit or receive apertures, or other factors. The definitions of test transmit apertures and test receive apertures used for the calibration process may be, but need not necessarily be the same as the definition of apertures used for normal imaging with the probe. Therefore, the phrase "test aperture" as used herein may refer to either a transmit test aperture or a receive test aperture unless otherwise specified.

In some embodiments, the test transmit aperture and the test receive aperture used during the process 400 of FIG. 6 may be substantially close to one another. For example, in some embodiments, the test transmit aperture and the test receive aperture may be within an expected coherence width of an intended imaging application relative to one another. For example, in some embodiments, a receive aperture may include all elements on a common array (e.g., elements sharing a common backing block). Alternatively, a receive aperture may comprise elements from two or more separate arrays. In further embodiments, a receive aperture may include a selected group of transducer elements along a large continuous array. In other embodiments, the test transmit aperture and the test receive aperture need not be close to one another, and may be spaced from one another by a distance greater than any anticipated coherence width. In further embodiments, if the phantom is known to have a uniform speed of sound, the coherence width need not be a significant consideration.

In some embodiments, a single transmit test aperture may be used to obtain both a reference image and data from which a test image may be formed. In such embodiments, a first receive aperture may be used to form a reference image, and a second (or third, etc.) receive aperture may be used to form or obtain test image data. Similarly, a single receive aperture may be used for obtaining both a reference image and data for a test image if different transmit apertures are used for the reference image and the test image data. Thus, the test transmit aperture and the test receive aperture need not necessarily be near one another. In other embodiments, reference images may be obtained using transmit and receive elements of a first array, while data for test images may be obtained using transmit and receive elements of a second array, where the second array is a test array to be calibrated.

As described above, in some embodiments, the step of obtaining reference data 402 may comprise retrieving reference data from a data storage device. Such a data storage device may be physically located within a calibration controller, within an ultrasound imaging system, within a probe, or on a separate storage device that may be accessible via a wired or wireless network connection. Alternatively, the step of obtaining reference data 402 may comprise imaging the phantom with a reference group of transducer elements.

In some embodiments, the step of insonifying the phantom with a test transmit aperture 404 may comprise transmitting one or more pings from one or more transmit elements of a transmit aperture. A single transmit aperture may typically comprise one, two, three or a small number of adjacent elements.

After each transmitted ping, returning echoes may be received by all receive elements of the test receive aperture, and the echo data may be digitized and stored 406 in a digital memory device. The memory device may be any volatile or non-volatile digital memory device in any physical location that is electronically accessible by a computing device performing the imaging and calibration processes.

The received echo data may then be beamformed and processed to form a test image 408. In some embodiments, the steps of insonifying the phantom from a test transmit aperture 404 and receiving echoes with a test receive aperture 405 may be repeated using multiple combinations of different transmit apertures and/or receive apertures, and images obtained 408 from such transmitting and receiving may be combined in a process referred to as image layer combining prior to proceeding to subsequent steps of the process 400.

In various embodiments, the error function may be determined from some difference between the phantom reference data (e.g., information known about the position of reflectors in the phantom) and an image of the phantom obtained with the test receive aperture. In some embodiments, the choice of error function may be based on characteristics of the phantom used, available processing capabilities, a chosen optimization method or many other factors.

In some embodiments, a modified least squares optimization method may be used to minimize an error function based on the square of an aggregated straight-line error distance between the expected reflector center and an imaged reflector center. For example, after forming an image of the phantom with the echoes received at a test receive aperture, the system may identify the location of each reflector in the image by identifying the brightest point in the image of approximately the expected size in approximately the expected location of each known reflector. Once each reflector is identified, an error between the imaged position and the expected position of each reflector may be determined. In some embodiments, these individual reflector-position errors may then be aggregated into a collective reflector pattern error, such as by summing all individual reflector errors. Alternatively, the individual errors may be aggregated using any other function, such as taking a maximum error, an average, or a weighted sum of individual errors. For example, if a phantom has some reflectors that are more difficult to detect than others, difficult-to-detect reflectors may be given less weight in the aggregate error function so as to obtain a more balanced result. In various embodiments, such individual and/or aggregate errors may be either scalar or vector quantities.

In some embodiments, reflector images may be sought within a predetermined search area surrounding the expected location of each reflector. The shape and size of a search area may be defined based on the known pattern of reflectors and the distance between reflectors. In some embodiments, images of reflectors may be identified by artificial intelligence or probability analysis using information about nearby reflectors and the known pattern of reflectors. In other embodiments, the search area surrounding each reflector may comprise a circular, rectangular or other geometric area centered on the point of a center of an expected reflector position. The size of a search area may be selected to be larger than the imaged reflectors, but typically small enough that adjacent search areas do not overlap.

In some embodiments, when the actual positions of reflectors in the phantom are known, this knowledge may be used to greatly simplify the process of forming an image of the phantom. For example, forming an image 408 may be limited to beamforming only echoes representing search areas surrounding the expected positions of reflectors in the phantom (rather than beamforming an entire image field). In other embodiments, beamforming may be limited to a search area defining the overall pattern of reflectors. For example, this may be accomplished in some embodiments by beamforming vertical and horizontal pixel bands slightly wider than the expected position of the pins in FIG. 1.

In some embodiments, the error function may be defined based on one or more simplifying assumptions. For example, instead of detecting and optimizing based on the two-dimensional or three-dimensional position of each individual reflector, a line or curve may be fit to the series of reflectors. For example, using the phantom layout shown in FIG. 1, a vertical line may be drawn through the pins spaced along the Y axis. In practice, reflectors in the approximate location of the vertical pins may be detected, a fit line through the detected reflectors may be calculated, and the quality of the fit line may be evaluated using a factor such as a coefficient of determination ($R^2$ value). An error function may then be defined based on the $R^2$ value of the line connecting the vertical pins. A similar approach may be taken for the horizontal pins. The simplifying assumption of pins fit to a line may ignore the spacing between the pins along the fit line, and may therefore be less precise than methods defining an error function based on two-dimensional position of each pin. However, optimizing based on a single line segment may be substantially faster in processing terms than optimizing based a plurality of individual pin reflector positions. Therefore, such simplifications may still provide valuable information in exchange for a faster processing time. In alternative embodiments, polynomial curves, circles or other mathematically-defined geometric shapes may be used as simplifications for representing a pattern of reflectors within a phantom.

In other embodiments, the error function may be defined as some quantity other than reflector position. For example, in some embodiments, an error function may be defined as a sum of absolute value differences in brightness of the individual imaged reflectors relative to a reference image. In another embodiment, an error function may be defined based on a complete collective reflector pattern. For example, a phantom may be designed to contain an array of reflectors representing a reference number in binary form (i.e., a reflector may represent a '1' and the absence of a reflector at a grid position may represent a '0'). In such embodiments, a calibration process may be configured to 'read' the binary values, and the error function may be defined as the number of bits different from the expected reference number. In further embodiments, an error function may be at least partially based on a pattern of "holes"—regions of the phantom that absorb the ultrasound energy. Many other error functions may also be used.

Figure 7:
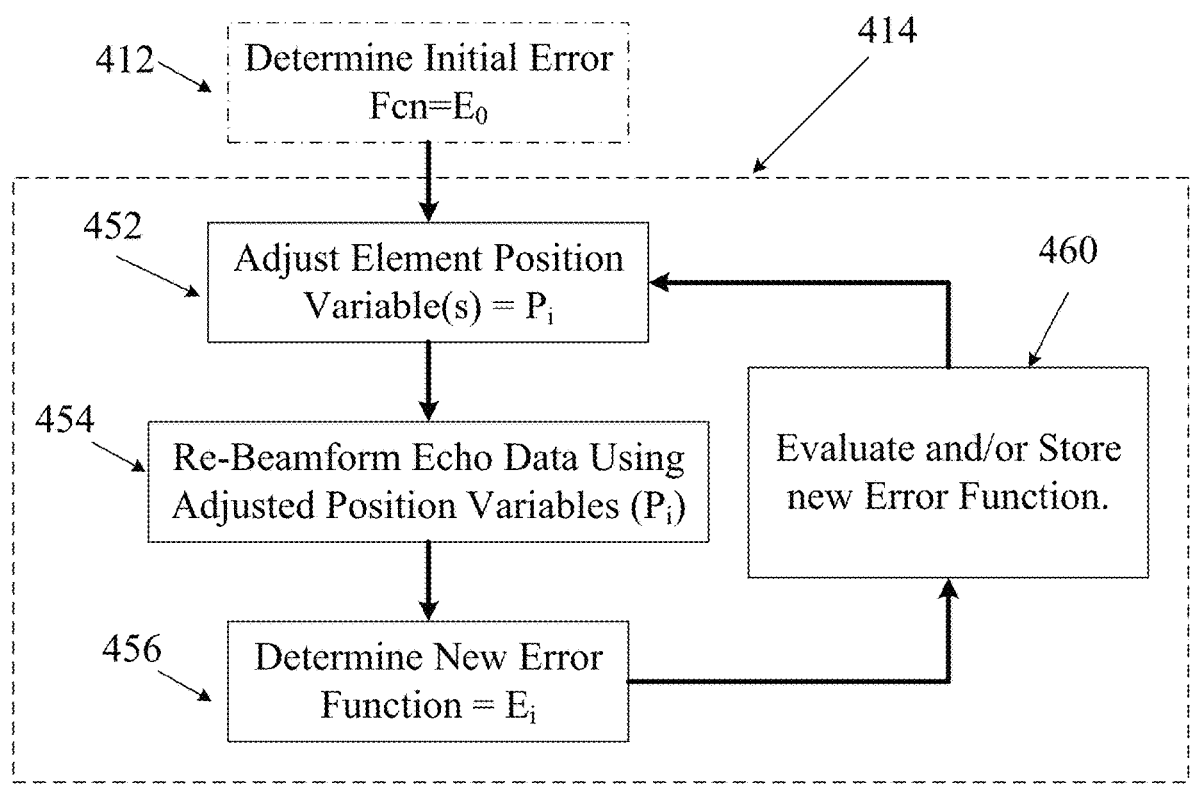
FIG. 7 is a process flow diagram illustrating one embodiment of an iterative optimization process for minimizing an error function by adjusting transducer element position variables.

FIG. 7 illustrates one embodiment of an iterative optimization process 414 for minimizing an error function by adjusting transducer element position variables. After determining an initial error function ($E_0$) in step 412, the process 414 may proceed to iteratively seek a minimum of an error function by making incremental adjustments to one or more variables describing the position of the elements of the test transmit and/or receive aperture. Thus, during a first iteration, the process may adjust 452 one or more initial test aperture element position variables ($P_0$) to obtain new test aperture element position variables ($P_1$). Without the need to re-insonify the phantom, the stored received echo data (from 406 in FIG. 6) may then be re-beamformed using the adjusted element position parameters 454 ($P_1$) (image layers may also be combined as needed during this step) in order to form a new image of the phantom. From the new image, a new error function ($E_1$) may be quantified 456 and then evaluated or stored 460 before returning to step 452 for a second iteration. The nature of the adjustments 452 and the error evaluations 460 may depend on the type of optimization routine being used.

In some embodiments, adjustments to the element position variables may be essentially random in each iteration (i.e., with no connection to adjustments made in prior iterations). Such random adjustments may be made within a predetermined range of values relative to current element position data based on expectations of the possible degree of mis-calibration of existing element position data. In the case of random adjustments, an error function obtained from each iteration may be stored, and a minimum error function may be identified by comparing the results of all iterations.

In other embodiments, adjustments may be directly based on information from previous iterations, such as an evaluation of the magnitude and/or direction of a change in the error value. For example, in some embodiments, if the new error function $E_1$ is less than the initial error function $E_0$, then the adjustment made in step 452 may be determined to be a good adjustment and the process may repeat for more iterations making further incremental adjustments to the position variable(s). If the new error function $E_1$ obtained in the first iteration is not less than the initial error function $E_0$ (i.e. $E_1 \geq E_0$), then it may be assumed that the adjustment of step 452 was made in the wrong direction. Thus, in a second iteration, during step 452, the original element position variable(s) $P_0$ may be adjusted in a direction opposite to that tried during the first iteration. If the resulting new error function $E_2$ is still not smaller than the initial error function $E_0$, then the error function is at a minimum (at least with respect to the adjusted element position variable(s)). In such a case, the error minimization process may be stopped, and the last good position variables may be stored as the new transducer element positions.

In some embodiments, the process 414 may be repeated through as many iterations as needed until the error function is minimized. In other embodiments, the process 414 may be stopped after a fixed number of iterations. As will be clear to the skilled artisan, multiple 'optimum' solutions may exist. As a result, in some embodiments, the iterative calibration process may be repeated multiple times, and the results of the several calibrations may be compared (automatically using image processing techniques or manually by a person) to identify a suitable solution. In any event, it is not necessary to identify the absolute optimal result.

In various embodiments, the position of transducer elements may be described by multiple variable quantities. Ultimately, it is desirable to know the acoustic position (which may be different than the element's apparent mechanical position) of each transducer element relative to some known coordinate system. Thus, in some embodiments, the acoustic position of each transducer element may be defined by an x, y, and z position (e.g., with reference to a Cartesian coordinate system 45 such as that shown in FIGS. 1-3). In adjusting such quantities during the optimization process 414, position variables may be adjusted individually or in groups.

Performing the optimization process by adjusting the x, y and z position of each transducer element may be somewhat computationally intensive, since a single aperture may contain hundreds of individual elements. This may result in the iterative adjustment of several hundred if not thousands of variables. This is particularly true for probes with 2D arrays (i.e., those with transducer elements spaced from one another in X and Z directions), curved 1D or 2D arrays (i.e., arrays with curvature about either the X or the Z axis), and 3D arrays (i.e., probes with curvature about two axes). While potentially computationally intensive, the various embodiments herein may be used to calibrate any ultrasound probe with large continuous planar or curved 1D or 2D arrays as well as large continuous 3D arrays with curvature about two axes.

As an alternative, some embodiments may employ one or more simplifying assumptions. For example, in some embodiments it may be assumed that element position relationships within a single array remain fixed relative to one another such that an array with a common backing block will only move, expand or contract uniformly. In some embodiments, it may also be assumed that the elements are uniformly distributed across the array. Using such assumptions, locating a center point of an array, a width of the array and an angle of the array surface relative to a known datum may provide sufficient information about the acoustic position of each element. For example (with reference to FIG. 1), the position of all elements in the left array 12 may be assumed based on overall array position variables, which may include array width (V), the position of the array's center (i) in the scan plane (i.e., the X-Y plane), and the angle of the array surface in the scan plane relative to some baseline (θ). If it is assumed that the acoustic centers of elements are uniformly distributed across the array with a consistent spacing in the X direction for a 1D array or in the X and Z directions for a 2D array, then the acoustic position of each transducer element may be mathematically expressed in terms of the above four variables (center-X, center-Y, width and angle). In some embodiments, if the array is a 2D array, a fifth variable describing the position of an array's center in the Z-direction (center-Z) may also be used. Alternatively, one or more of these variables may be treated as fixed in some embodiments. Using such simplifications, an error function minimizing process need only iteratively optimize four or five transducer element position variables. In the case of different probe constructions, different simplifying assumptions may also be used.

In some embodiments two or more optimization processes may be combined in parallel or sequential processes in order to improve processing efficiency, calibration precision, or both. For example, in one embodiment, a two-stage optimization process may be used in which a first stage provides a coarse improvement to element position variables while relying on one or more simplifying assumptions. A second stage may then provide a more detailed improvement to the element position variables while relying on fewer simplifying assumptions, but starting from the improved information obtained during the first stage. During a first stage of one example embodiment, multiple reflectors may be represented with a single geometric shape such as a line, and the spacing between transducer elements may be treated as fixed (i.e., such values are not varied during the optimization). A second stage process may then be performed, in which the position of each pin is optimized by varying element position variables including the spacing between transducer elements.

In some embodiments, a similar calibration process may be used to calibrate a probe 55 with a large continuous array 18, such as that illustrated in FIG. 2. Because the continuous array 18 lacks physical separations, the same simplifying assumptions discussed above with regard to the probe of FIG. 1 may not apply. Instead, the probe 55 of FIG. 2 may be calibrated by making simplifying assumptions about the shape of the large array, and apertures may be defined by using relatively small groups of elements at various positions along the array. In some embodiments, the x-y position of each element in an aperture may be used as element position parameters to be optimized. Such selected apertures may then be calibrated in substantially the same manner described above.

Regardless of the number of variables to be optimized in the iterative error function minimizing process 414, element position variables may be adjusted 452 either in series or in parallel. For example, in embodiments in which position variables are to be adjusted in series, only one variable may be adjusted during each iteration. In some embodiments of serial optimization, a single variable may be optimized (i.e., the error function may be minimized by adjusting only that single variable) before proceeding to the next variable. In embodiments in which two or more position variables are to be adjusted in parallel, the two or more variables may each be adjusted during each iteration. In some embodiments, those two variables may be optimized before proceeding to optimization of other variables. Alternatively, all variables may be optimized in parallel. In other embodiments, position variables may be optimized using a combination of series and parallel approaches. It should be noted this distinction between series and parallel optimization approaches should not be confused with parallel computer processing. Depending on computing hardware used, even optimizations performed in series as described above may be computed simultaneously using separate threads in parallel processors.

After completing calibration of a first array or aperture, the process of FIG. 6 may be repeated for each remaining array or aperture individually. For example, using the three-array probe of FIG. 1, the calibration process may be repeated for the right array 14 and then again for the left array 12. After determining updated element position data for the first array, updated element position data for each subsequently-tested array may be determined and stored relative to a common coordinate system such that the position of any element in the probe may be determined relative to any other. For example, the calibration process may determine the center of the center array, which may be used as the center of the coordinate system for the other arrays. The angle of the center array may also be used as a datum against which angles of the other arrays may be defined. In other embodiments, the positions and orientations of the apertures may be determined relative to some other datum independent of any array. In other embodiments, element positions may ultimately be defined using any coordinate system centered around any point relative to the probe.

In some embodiments, transducer element position adjustments may be obtained and stored in the form of new corrected element position coordinates. In other embodiments, position adjustments may be obtained and stored as coefficients to be added to or multiplied with previous element position coordinates. For example, in some embodiments "factory" element position data may be stored in a read-only memory device in a location readable by an ultrasound system, such as a ROM chip within a probe housing. Such factory position data may be established at the time of manufacturing the probe, and subsequent calibration data may be stored as coefficients that may be applied as adjustments to the factory position data.

In some embodiments, adjusted element position data for each transducer element in a probe may be stored in a non-volatile memory device located within a probe housing. In other embodiments, adjusted element position data may be stored in a non-volatile memory device located within an imaging system, on a remote server, or in any other location from which the information may be retrieved by an imaging system during image beamforming.

In some embodiments, a calibration process using the methods described above, may be particularly useful in rapidly re-calibrating an adjustable probe such as that illustrated in FIG. 3. Generally, an "adjustable probe" may be any ultrasound imaging probe in which the position and/or orientation of one or more transducer arrays or transducer elements may be changed relative to one or more other transducer arrays or elements. Many adjustable probe configurations beyond that shown in FIG. 3 are possible and may be designed for specific imaging applications.

In some embodiments, one or more of the arrays in an adjustable probe may be permanently secured to the housing in a fixed orientation and position (e.g., the center array or the left or right end array), while the remaining arrays may be movable to conform to a shape of an object to be imaged. The fixed array would then be in a permanently known position and orientation. Alternatively, the position and orientation of one or more arrays may be known based on one or more position sensors within an adjustable probe. The known-position array(s) may then be used to obtain a reference image of a phantom (or even a region of an object or patient to be imaged), and an optimization process may be used to determine an adjusted position of the movable arrays. For example, a sonographer may adjust the adjustable arrays of an adjustable probe to conform to a patient's anatomy. Then, during normal imaging, a reference image may be obtained using the known array, and positions of the remaining arrays may be determined by an optimization routine configured to minimize an error function (e.g., using an optimization routine as described above) defining an error between the reference image obtained from the center array and images obtained from each adjustable array.

In other embodiments, a sonographer may adjust the arrays of an adjustable probe to conform to a patient's anatomy. The sonographer may then place the probe onto a phantom that includes a conformable section configured to receive the probe in its adjusted position. For example, a conformable section may include a flexible bag containing a liquid or gel selected to transmit ultrasound signals at substantially the same speed of sound as the material of the phantom. A calibration process may then be initiated, and the position of each adjustable array may be determined by an iterative optimization routine in which reference data describing the phantom is compared with images of the phantom obtained with each array.

In some embodiments, the element-position information may change between performing a calibration operation and capturing raw ultrasound data. For example, a probe may be dropped, damaged or may be otherwise altered (such as by thermal expansion or contraction due to a substantial temperature change) before or during a raw sample data capture session. In some embodiments, the probe may be re-calibrated using captured, stored raw echo data as described below.

Figure 8:
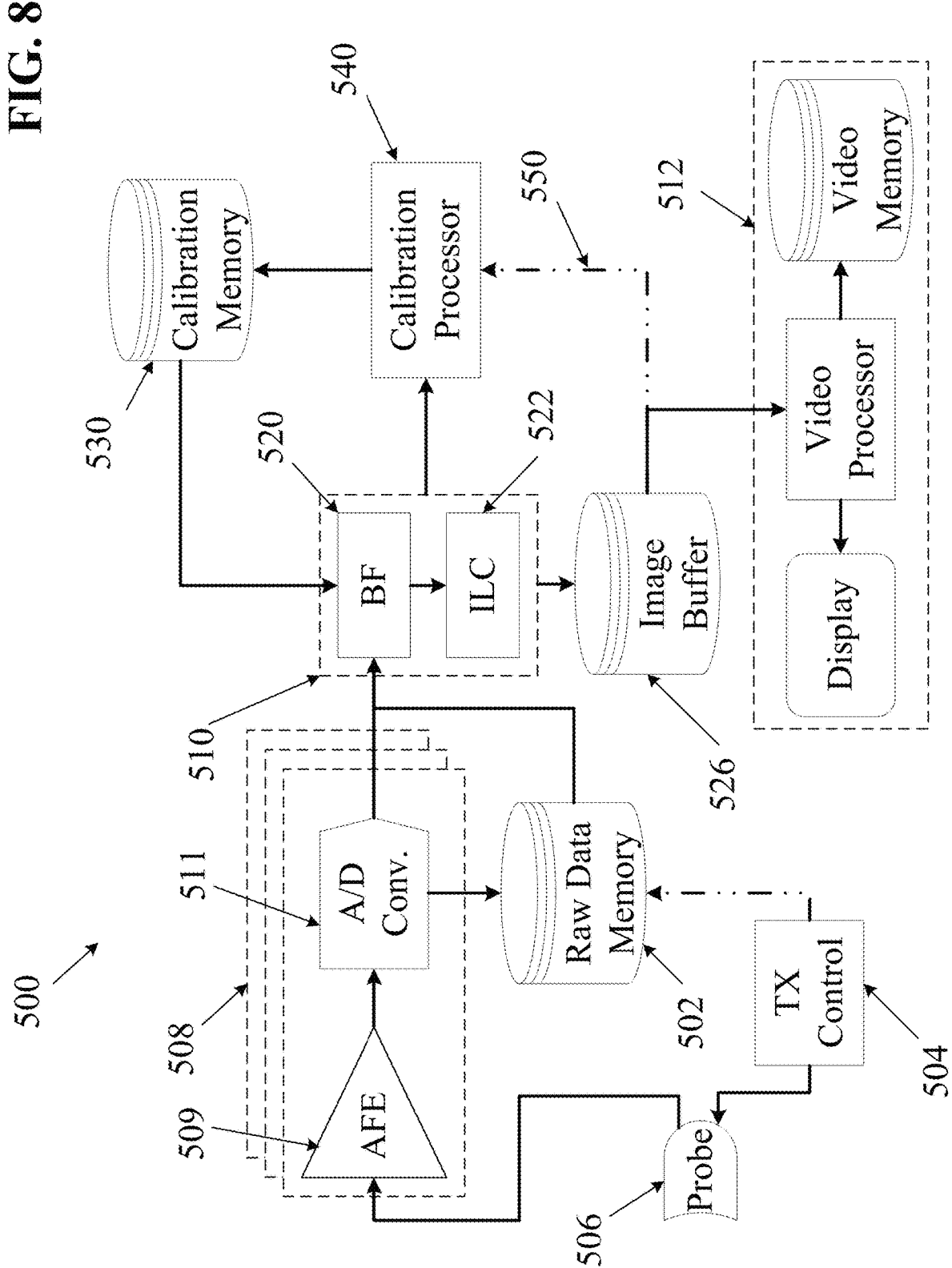
FIG. 8 is a block diagram illustrating components of an ultrasound imaging system in accordance with some embodiments.

In other embodiments, a calibration system may be incorporated into an ultrasound imaging system. In some embodiments, as shown for example in FIG. 8, an ultrasound imaging system 500 may include a raw data memory device 502 configured to capture and store raw, un-beamformed echo data. As shown in FIG. 8 an ultrasound imaging system configured to perform an optimization-based calibration may include a transmit control subsystem 504, a probe subsystem 506, a receive subsystem 508, an image generation subsystem 510, a video subsystem 512, a calibration memory 530 and a calibration processor 540. The image generation subsystem may include a beamformer 520 (hardware or software) and an image-layer combining block 522.

In some embodiments, a calibration system may be provided independently of an imaging system. In such embodiments, components such as the video subsystem 512 may be omitted. Other components shown in FIG. 8 may also be omitted where practicable.

In practice, the transmit control subsystem 504 may direct the probe to transmit ultrasound signals into a phantom. Echoes returned to the probe may produce electrical signals which are fed into the receive sub-system 508, processed by an analog front end, and converted into digital data by an analog-to-digital converter. The digitized echo data may then be stored in a raw data memory device 502. The digital echo data may then be processed by the beamformer 520 in order to determine the location of each reflector so as to form an image. In performing beamforming calculations, the beamformer may retrieve calibration data from a calibration memory 530. The calibration data may describe the position of each transducer element in the probe. In order to perform a new calibration, the calibration processor may receive image data from the image formation block 520 or from an image buffer memory device 526 which may store single image frames and/or individual image layers.

The calibration processor may then perform an optimization-based calibration routine. Once a calibration process is complete, new calibration information may be stored in the calibration memory device 530 for use in subsequent imaging processes or in additional calibration processes.

Using such a system, raw echo data of a phantom may be captured and stored along with raw echo data from a target object imaging session (e.g., with a patient). Capturing and storing raw echo data of a phantom before and/or after an imaging session may allow for later optimization of the imaging-session data. Such optimization may be applied at any point after the imaging session using the stored raw data and the methods described above.

As shown in FIG. 8, an ultrasound imaging system 500 may comprise an ultrasound probe 506 which may include a plurality of individual ultrasound transducer elements, some of which may be designated as transmit elements, and others of which may be designated as receive elements. In some embodiments, each probe transducer element may convert ultrasound vibrations into time-varying electrical signals and vice versa. In some embodiments, the probe 506 may include any number of ultrasound transducer arrays in any desired configuration. A probe 506 used in connection with the systems and methods described herein may be of any configuration as desired, including single aperture and multiple aperture probes.

The transmission of ultrasound signals from elements of the probe 506 may be controlled by a transmit controller 504. Upon receiving echoes of transmit signals, the probe elements may generate time-varying electric signals corresponding to the received ultrasound vibrations. Signals representing the received echoes may be output from the probe 506 and sent to a receive subsystem 508. In some embodiments, the receive subsystem 508 may include multiple channels. Each channel may include an analog front-end device ("AFE") 509 and an analog-to-digital conversion device (ADC) 511. In some embodiments, each channel of the receive subsystem 508 may also include digital filters and data conditioners (not shown) after the ADC 511. In some embodiments, analog filters prior to the ADC 511 may also be provided. The output of each ADC 511 may be directed into a raw data memory device 502. In some embodiments, one independent channel of the receive subsystem 508 may be provided for each receive transducer element of the probe 506. In other embodiments, two or more transducer elements may share a common receive channel.

In some embodiments, the ultrasound imaging system may store digital data representing the timing, phase, magnitude and/or the frequency of ultrasound echo signals received by each individual receive element in a raw data memory device 502 before performing any further beamforming, filtering, image layer combining or other image processing.

In addition to received echo data, information about one or more ultrasound transmit signals that generated a particular set of echo data may also be stored in a memory device, such as the raw data memory device 502 or another memory device. For example, when imaging with a multiple aperture ping ultrasound method as described above, it is desirable to know information about a transmitted ping that produced a particular set of echoes. Such information may include the identity and/or position of one or more a transmit elements as well as a frequency, magnitude, duration or other information describing a transmitted ultrasound signal. Transmit data is collectively referred herein to as "TX data". In some embodiments, such TX data may be stored explicitly in the same raw data memory device in which raw echo data is stored. For example, TX data describing a transmit signal may be stored as a header before or as a footer after a set of raw echo data generated by the transmit signal. In other embodiments, TX data may be stored explicitly in a separate memory device that is also accessible to a system performing a beamforming process. In embodiments in which transmit data is stored explicitly, the phrases "raw echo data" or "raw data" may also include such explicitly stored TX data.

TX data may also be stored implicitly. For example, if an imaging system is configured to transmit consistently defined ultrasound signals (e.g., consistent magnitude, shape, frequency, duration, etc.) in a consistent or known sequence, then such information may be assumed during a beamforming process. In such cases, the only information that needs to be associated with the echo data is the position (or identity) of the transmit transducer(s). In some embodiments, such information may be implicitly obtained based on the organization of raw echo data in a raw data memory.

For example, a system may be configured to store a fixed number of echo records following each ping. In such embodiments, echoes from a first ping may be stored at memory positions 0 through 'n' (where 'n' is the number of records stored for each ping), and echoes from a second ping may be stored at memory positions n+1 through 2n+1. In other embodiments, one or more empty records may be left in between echo sets. In some embodiments received echo data may be stored using various memory interleaving techniques to imply a relationship between a transmitted ping and a received echo data point (or a group of echoes). In general, a collection of echo records corresponding to echoes of a single transmitted ping received by a single receive element may be referred to herein as a single "echo string." A complete echo string may refer to all echoes of the single ping received by the receive element, whereas a partial string may refer to a sub-set of all echoes of the single ping received by the receive element.

Similarly, assuming data is sampled at a consistent, known sampling rate, the time at which each echo data point was received may be inferred from the position of that data point in memory. In some embodiments, the same techniques may also be used to implicitly store data from multiple receive channels in a single raw data memory device.

In other embodiments, the raw echo data stored in the raw data memory device 520 may be in any other structure as desired, provided that a system retrieving the echo data is able to determine which echo signals correspond to which receive transducer element and to which transmitted ping. In some embodiments, position data describing the position of each receive transducer element may be stored in the calibration memory device along with information that may be linked to the echo data received by that same element. Similarly, position data describing the position of each transmit transducer element may be stored in the calibration memory device along with information that may be linked to the TX data describing each transmitted ping.

In some embodiments, each echo string in the raw data memory device may be associated with position data describing the position of the receive transducer element that received the echoes and with data describing the position of one or more transmit elements of a transmit aperture that transmitted the ping that produced the echoes. Each echo string may also be associated with TX data describing characteristics of the transmitted ping.

In some embodiments, a probe may be calibrated using raw echo data stored in a memory device without raw data of a phantom image. Assuming at least one array (or one portion of an array) is known or assumed to be well-calibrated, nearly any image data with a pattern of strong reflectors may be used to calibrate second, third or further arrays or array segments. For example, echo data from the known-calibrated aperture, array or array segment may be beamformed to obtain a reference image. Stored echo data from the remaining apertures/arrays may then be calibrated using any of the methods described above to calibrate the position of the remaining arrays, apertures or array segments relative to the first. By performing a calibration process using stored echo data, a probe may be calibrated even when neither the probe itself nor the patient (or other imaged object) is physically present proximate to the device performing the re-beamforming and image processing. In such embodiments, the steps of insonifying a phantom 404, and receiving echoes 405 may be omitted from the process 400 of FIG. 6 at the time of a calibration process, since those steps were performed during the imaging session in which the raw data was captured.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. As used herein, unless explicitly stated otherwise, the term "or" is inclusive of all presented alternatives, and means essentially the same as the commonly used phrase "and/or." Thus, for example the phrase "A or B may be blue" may mean any of the following: A alone is blue, B alone is blue, both A and B are blue, and A, B and C are blue. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. An ultrasound probe calibration system, comprising:
    an ultrasound probe having a plurality of transmit transducer elements and a plurality of receive transducer elements;
    a phantom having a pattern of reflectors;
    a first memory device containing reference data describing the pattern of reflectors of the phantom;
    a second memory device containing transducer element position data describing a position of each transmit transducer element and each receive transducer element relative to a common coordinate system; and
    an imaging control system containing calibration program code configured to direct the system to:
        insonify the phantom with a single spherical wavefront from a first transmit transducer element of the plurality of transmit transducer elements, receive echo data from the single spherical wavefront with two or more of the receive transducer elements, and store echo data in a third memory device, form a first plurality of complete images of the pattern of reflectors with echo data received by each of the two or more receive transducer elements and transducer element position data, form a first combined image of the pattern of reflectors by combining the first plurality of complete images, determine measurement data describing a position of the pattern of reflectors as indicated by the first combined image, quantify an error between the measurement data and the reference data, and iteratively optimize the transducer element position data based on the quantified error;

wherein the imaging control system is configured to iteratively optimize the phantom by:

adjusting the transducer element position data;

forming a second plurality of complete images of the pattern of reflectors by re-beamforming the stored echo data using the adjusted transducer element position data;

forming a second combined image of the pattern of reflectors by combining the second plurality of complete images;

quantifying a second error based on the second combined image; and evaluating the second error to determine whether the adjusted transducer element position data improves the image.

2. The system of claim 1, wherein the reference data is based on physical measurements of the phantom.

3. The system of claim 1, wherein the reference data is based on a reference image.

4. The system of claim 1, wherein the imaging control system is configured to iteratively optimize the transducer element position data using a least squares optimization process.

5. The system of claim 1, wherein the phantom further comprises at least one region that absorbs ultrasound signals.

6. The system of claim 1, wherein the ultrasound probe comprises a plurality of transducer arrays.

7. The system of claim 1, wherein the ultrasound probe comprises a single continuous transducer array.

8. The system of claim 1, wherein the ultrasound probe comprises a transducer array with a concave curvature.

9. The system of claim 1, wherein the phantom comprises a pattern of pins.

10. The system of claim 1, wherein the phantom comprises living tissue.

11. The system of claim 1, wherein the calibration program code is configured to determine measurement data by fitting a curve to a detected pattern of reflectors.

12. The system of claim 11, wherein the calibration program code is configured to quantify an error by determining a coefficient of determination quantifying a degree of fit of the curve.

13. The system of claim 1, wherein at least two of the first memory device, the second memory device, and the third memory device are logical portions of a single physical memory device.

14. An ultrasound probe calibration system, comprising:

an ultrasound probe having a plurality of transmit transducer elements and a plurality of receive transducer elements;

a phantom having a pattern of reflectors;

a first memory device containing reference data describing the pattern of reflectors of the phantom;

a second memory device containing transducer element position data describing a position of each transmit transducer element and each receive transducer element relative to a common coordinate system; and an imaging control system containing calibration program code configured to direct the system to:

insonify the phantom with the transmit transducer elements, receive echo data with the receive transducer elements, and store echo data in a third memory device, form a first image of the pattern of reflectors by beamforming the stored echo data using the transducer element position data, determine measurement data describing a position of the pattern of reflectors as indicated by the first image, quantify an error between the measurement data and the reference data, and iteratively optimize the transducer element position data based on the quantified error;

wherein the imaging control system is configured to iteratively optimize the phantom by:

adjusting the transducer element position data;

forming a second image of the pattern of reflectors by re-beamforming the stored echo data using the adjusted transducer element position data;

quantifying a second error based on the second image; and evaluating the second error to determine whether the adjusted transducer element position data improves the image.

15. The system of claim 14, wherein the reference data is based on physical measurements of the phantom.

16. The system of claim 14, wherein the reference data is based on a reference image.

17. The system of claim 14, wherein the imaging control system is configured to iteratively optimize the transducer element position data using a least squares optimization process.

18. The system of claim 14, wherein the phantom further comprises at least one region that absorbs ultrasound signals.

19. The system of claim 14, wherein the ultrasound probe comprises a plurality of transducer arrays.

* * * * *